(12) United States Patent
Namba et al.

(10) Patent No.: US 9,243,048 B2
(45) Date of Patent: Jan. 26, 2016

(54) DECREASING CANCER CELL PROLIFERATION WITH WNT REMAINING ACTIVE

(75) Inventors: Masayoshi Namba, Okayama (JP); Toshiya Tsuji, Okayama (JP)

(73) Assignee: Hiromi Kumon, Okayama (JP)

( * ) Notice: Subject to any disclaimer, the term of this patent is extended or adjusted under 35 U.S.C. 154(b) by 329 days.

(21) Appl. No.: 12/318,900

(22) Filed: Jan. 12, 2009

(65) Prior Publication Data

US 2010/0204308 A1 Aug. 12, 2010

Related U.S. Application Data

(60) Continuation of application No. 11/434,813, filed on May 17, 2006, now abandoned, which is a division of application No. 10/130,360, filed as application No. PCT/JP00/05879 on Aug. 30, 2000, now abandoned.

(30) Foreign Application Priority Data

Nov. 19, 1999 (JP) ..................... 99-330604

(51) Int. Cl.
| | |
|---|---|
| *A61K 48/00* | (2006.01) |
| *A61K 35/00* | (2006.01) |
| *C07K 14/47* | (2006.01) |
| *A61K 35/761* | (2015.01) |
| *A61K 35/76* | (2015.01) |
| *A61K 38/00* | (2006.01) |

(52) U.S. Cl.
CPC ............. *C07K 14/4703* (2013.01); *A61K 35/76* (2013.01); *A61K 35/761* (2013.01); *A61K 38/00* (2013.01); *A61K 48/00* (2013.01); *A61K 48/0016* (2013.01); *A61K 48/0058* (2013.01); *A61K 48/0075* (2013.01)

(58) Field of Classification Search
CPC ... A61K 31/7088; A61K 38/00; A61K 48/00; A61K 35/761; C07K 14/4703
See application file for complete search history.

(56) References Cited

U.S. PATENT DOCUMENTS 6,344,541 B1 * 2/2002 Bass et al. ................. 530/324

FOREIGN PATENT DOCUMENTS

| WO | WO 98/27932 A2 | 7/1998 |
|---|---|---|
| WO | WO 98/46755 A1 | 10/1998 |
| WO | WO 99/14328 A | 3/1999 |
| WO | WO 00/18914 A2 | 4/2000 |

OTHER PUBLICATIONS

Fujita et al, Biochem Biophys Res Comm, 238: 658-664, 1997).*
Of Recchia et al (Proc Natl Acad Sci, Mar. 16, 1999; 96(6): 2615-2620).*
Hodgson et al (J Mol Med, 75: 249-258, 1997).*
Sheu et al., "Loss of Heterozygosity and Microsatellite Instability in Hepatocellular Carcinoma in Taiwan," British Journal of Cancer (1996) 30(3/4), pp. 468-476.
El-Naggar et al., "Allelic Loss and Replication Errors at Microsatellite Loci on Chromosome 11p in Head and Neck Squamous Carcinoma: Association with Aggressive Biological Features," Clinical Cancer Research, vol. 2, May 1996, pp. 903-907.
Dahiya et al., "Deletion of Chromosome 11p15, p12, q22, q23-24 Loci in Human Prostate Cancer," Int. J. Cancer: 72 (1997) pp. 283-288.
Bai et al., "Immortalization of Normal Human Fibroblasts by Treatment with 4-Nitroquinoline 1-Oxide," Int. J. Cancer: vol. 53 (1993) pp. 451-456.
Reid et al., "Localization of a Tumor Suppressor Gene in 11p15.5 Using the G401 Wilms' Tumor Assay," Human Molecular Genetics, vol. 5, No. 2 (1996) pp. 239-247.
Miyake et al., "Efficient Generation of Recombinant Adenoviruses Using Adenovirus DNA-Terminal Protein Complex nada Cosmid Bearing the Full-Length Virus Genome," Proc. Natl. Acad. Sci., vol. 93, Feb. 1996, pp. 1320-1324.
Leiber et al., "Recombinant Adenoviruses with Large Deletions Generated by Cre-Mediated Excision Exhibit Different Biological Properties Compared with First-Generation Vectors in Vitro and In Vivo," Journal of Virology, vol. 70, Dec. 1996, pp. 8944-8960.
Mizuguchi et al., "A Simple Method of Constructing E1-and E1/E4-Deleted Recombinant Adenovrial Vectors," Human Gene Therapy, vol. 10, Aug. 10, 1999, pp. 2013-2017.
Steinwaerder et al., "Generation of Adenovirus Vectors Devoid of All Viral Genes by Recombinant Between Inverted Repeats," Journal of Virology, vol. 73, Nov. 1999, pp. 9303-9312.
Recchia et al., "Site-Specific Integration Mediated by a Hybrid Adenovirus/Adeno-Associated Virus Vector," Proc. Natl. Acad. Sci., vol. 96, pp. 2615-2620.
Mizuguchi et al., "Technique for Constructing Recombinant Adenovirus Vectors and Application for Next Generation Vectors," T.N. Nippon Rinsho, 7, 1544 (2000).
Namba et al., "Neoplastic Transformation of Human Diploid Fibroblasts (KMST-6) by Treatment with $^{60}$Co Gamma Rays," Int. J. Cancer: 35, pp. 275-280 (1985).
Mihara et al., "Immortalization of Normal Human Fibroblasts by Treatment with 4-Nitroquinoline 1-Oxide," Int. J. Cancer: 53, pp. 451-456 (1993).
Maruyama et al., "Oligo-capping: A Simple Method to Replace the Cap Structure of Eukaryotic mRNAs with Oligoribonucleotides," Gene, 138 (1994), pp. 171-174.
Winqvist et al., "Refinement of Regional Loss of Heterozygosity for Chromosome 11;15.5 in Human Breast Tumors," Cancer Research, 53, Oct. 1, 1993, pp. 4486-4488.

(Continued)

*Primary Examiner* — Deborah Crouch
*Assistant Examiner* — Magdalene Sgagias
(74) *Attorney, Agent, or Firm* — Fitch, Even, Tabin & Flannery LLP

(57) ABSTRACT

The genes the expression of which is reduced or disappeared in immortal cells including cancer cells are isolated, their DNA sequences are determined, the genes are expressed to produce cell proliferation inhibitory proteins, and the genes and the proteins are utilized as agents for diagnosis or treatment, including the genetic diagnosis of or the gene therapy of diseases such as cancer.

17 Claims, 15 Drawing Sheets

(56) References Cited

OTHER PUBLICATIONS

Dolan et al., "Allelotype Analysis of Oesophageal Adenocarcinoma: Loss of Heterozygosity Occurs at Multiple Sites," British Journal of Cancer (1996)78(7), pp. 950-957.

Baffa et al.., "Loss of Heterozygosity for Chromosome 11 in Adenocarcinoma of the Stomach," Cancer Research 56, (Jan. 15, 1996) pp. 268-272.

Namba et al., "Immortalization of Human Cells and Its Mechanisms," Critical Reviews™ in Oncogenesis, 7(1&2): pp. 19-31 (1996).

Li et al., "Intracerebral Adenovirus-Mediated *p53* Tumor Suppressor Gene Therapy for Experimental Human Glioma," Clinical Cancer Research, vol. 5, pp. 637-642, Mar. 1999.

Noda et al., "Cloning of Senescent Cell-Derived Inhibitors of DNA Synthesis Using an Expression Screen," Experimental Cell Research, 211, pp. 90-98 (1994).

Banga et al., "*SEN6*, a Locus for SV40-Mediated Immortalization of Human Cells, Maps to 6q26-27," Oncogene (1997), vol. 14, pp. 313-321.

Sandhu et al., "A Gene on 6q 14-21 Restores Senescence to Immortal Ovarian Tumor Cells," Oncogene (1996), vol. 12, pp. 247-252.

Garkavtsev et al., "Extension of the Replicative Life Span of Human Diploid Fibroblasts by Inhibition of the $p33^{ING1}$ Candidate Tumor Supressor," Molecular and Cellular Biology, Apr. 1997, pp. 2014-2019.

Shibanuma et al., "Induction of Senescence-Like Phenotypes by Forced Expression of *hic*-5, Which Encodes a Novel LIM Motif Protein, in Immortalized Human Fibroblasts," Molecular and Cellular Biology, Mar. 1997, pp. 1224-1235.

Krupnik et al., "Functional and Structural Diversity of the Human Dickkopf Gene Family," Gene 238 (1999), pp. 301-313.

Cadigan et al., Wnt Signaling: A Common Theme in Animal Development, Genes & Development, vol. 11, pp. 3286-3305.

Ligon et al., "Differentially Expressed Gene Products in Glioblastoma Cells Suppressed for Tumorigenicity," Journal of NeuroVirology (1998), vol. 4, pp. 217-226.

Lalande, "Parental Imprinting and Human Disease," Annv. Rev. Genet., 1997, vol. 30, pp. 173-195.

Feinberg, "Imprinting of a Genomic Domain o 11p15 and Loss of Imprinting in Cancer: An Introduction," Cancer Research (Suppl), 59, Apr. 1, 1999, pp. 1743s-1746s.

O'Briant et al., "Growth Inhibition of Human Lung Adenocarinoma Cell Line by Genetic Complementation with Chromosome 11," Anticancer Research, vol. 17 (1997), pp. 3243-3253.

Zhang et al., "New Progress in Gene Therapy—Human Gene Therapy Using Adenovirus Vector," Bullentin of Biology, vol. 29, No. 9, pp. 5-8 (1994).

Greco et al., "Delivery, Delivery, Delivery," Cancer Gene Therapy, Frontiers in Bioscience, vol. 7 (2002) pp. 1516-1524.

Zhou et al., "Challenges and Strategies: The Immune Responses in Gene Therapy," Medicinal Research Reviews, vol. 24, No. 6 (2004) pp. 748-761.

Seth et al., "A Recombinant Adenovirus Expressing Wild Type p53 Induces Apoptosis in Drug-Resistant Human Breast Cancer Cells: A Gene Therapy Approach for Drug-Resistant Cancers," Cancer Gene Ther., Nov.-Dec. 1997, 4(6), pp. 383-390.

Fujiwara et al., "Therapeutic Effect of a Retroviral Wild-Type p53 Expression Vector in an Orthotopic Lung Cancer Model," J National Cancer Institute, 86(19), Oct. 1994, pp. 1437-1438.

Woll et al., "Gene Therapy for Lung Cancer," Ann Oncol., 6 Suppl 1:73-7 (1995).

Badie et al., "Adenovirus-Mediated p53 Gene Delivery Inhibits 9L Glioma Growth in Rats," Neurol Res., 17(3), Jun. 1995, pp. 209-216.

Santoso et al., "Adenovirus-Based p53 Gene Therapy in Ovarian Cancer," Gynecol Oncol., 59(2), Nov. 1995, pp. 171-178.

Eastham et al., "In Vivo Gene Therapy with p53 or p21 Adenovirus for Prostate Cancer," Cancer Res., 55(22), Nov. 1995, pp. 5151-5155.

Roth et al., "Retrovirus-Mediated Wild-Type p53 Gene Transfer to Tumors of Patients with Lung Cancer," Nat Med, 2(9), Sep. 1996, pp. 985-991.

Hsiao et al., "Intracavitary Liposome-Mediated p53 Gene Transfer Into Glioblastoma with Endogenous Wild-Type p53 in Vivo Results in Tumor Suppression and Long-Term Survival," Biochem Biophys Res Commun, 233(s), Apr. 17, 1997, pp. 359-364.

Nguyen et al., "Delivery of the p53 Tumor Suppressor Gene Into Lung Cancer Cells by an Adenovirus/DNAComplex," Cancer Gene Ther, 4(3), May-Jun. 1997, pp. 191-198.

Asgari et al., "Inhibition of the Growth of Pre-Established Subcutaneous Tumor Nodules of Human Prostate Cancer Cells by Single Injection of the Recombinant Adenovirus p53 Expression Vector," Int J Cancer, 71(3), May 1997,pp. 377-382.

Qazilbash et al., "Cancer Gene Therapy Using a Novel Adeno-Associated Virus Vector Expressing Human Wild-Type p53," Gene Tehr., 4(7, Jul. 1997, pp. 675-682.

Cristiano, "Viral and Non-Viral Vectors for cancer Gene Therapy," Anticancer Res., 18(5A), Sep.-Oct. 1998, pp. 3241-3245.

Kim et al., "Intraperitoneal Gene Therapy with Adenoviral-Mediated p53 Tumor Suppressor Gene for Ovarian Cancer Model in Nude Mouse," Cancer Gene Ther., 6(2), Mar.-Apr. 1999, pp. 172-178.

Fujita et al., Biochem. Biophys. Res. Comm. 238:658-664.

\* cited by examiner

Fig.1

```
REIC     1   MQRLGATLLC LLLAAAVPTA PAPAPTATSA PVKPGPALSY PQEEATLNEM
hDkk3    1   ---------- ---------- ---------- ---------- ----------
RIG7-1

REIC    51   FREVEELMED TQHKLRSAVE EMEAEEAAAK ASSEVNLANL PPSYHNETNT
hDkk3   51   ---------- ---------- ---------- ---------- ----------
RIG7-1

REIC   101   DTKVGNNTIH VHREIHKITN NQTGQMVFSE TVITSVGDEE GRRSHECIID
hDkk3  101   ---------- ---------- ---------- ---------- ----------
RIG7-1

REIC   151   EDCGPSMYCQ PASFQYTCQP CRGQRMLCTR DSECCGDQLC VWGHCTKMAT
hDkk3  151   ---------- ---------- ---------- ---------- ----------
RIG7-1    1       ---- ---------- ---------- ---------- ----------

REIC   201   RGSNGTICDN QRDCQPGLCC AFQRGLLFPV CTPLPVEGEL CHDPASRLLD
hDkk3  201   ---------- ---------- ---------- ---------- ----------
RIG7-1   45  ---------- ---------- ---------- ---------- ----------

REIC   251   LITWELEPDG ALDRCPCASG LLCQPHSHSL VYVCKPTFVG SRDQDGEILL
hDkk3  251   ---------- ---------- ---------- ---------- ----------
RIG7-1   95  ---------- ---------- ---------- ---------- ----------

REIC   301   PREVPDEYEV GSPMEEVRQE LEDLERSLTE EMALGEPAAA AAALLGGEEI
hDkk3  301   ---------- ---------- ---------- ---------- ----------
RIG7-1  145  --------KL AASWRRCARS WRTWRGA
```

Fig.6
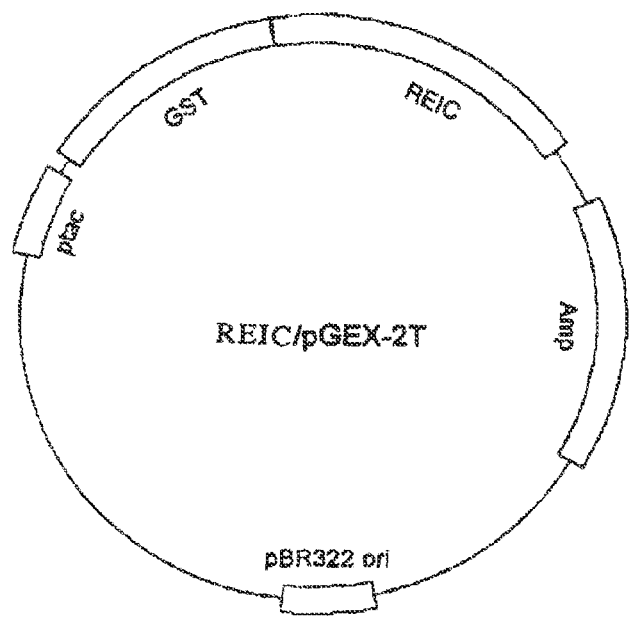
Fig.7
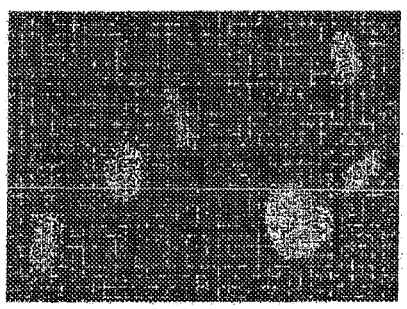 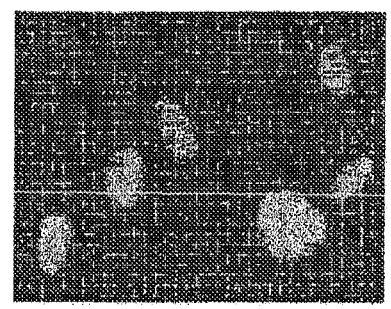
Rabbit Anti-REIC          Hoechst 33258

Fig.10

```
REIC cDNA : 2406 aatatgcgactgcgaacactgaactctacgccactccacaaatgatgtttcaggtgtca 2465
                 ||||||||||||||||||||||||||||||||||||||||||||||||||||||||||||
D11S2388  :  203 aatatgcgactgcgaacactgaactctacgccactccacaaatgatgtttcaggtgtca  144

REIC cDNA : 2466 tggactgttgccaccatgtattcatccagagttcttaaagtttaaagttgcacatgattg 2525
                 ||||||||||||||||||| ||||||||||||||||||||||||||||||||||||||||
D11S2388  :  143 tggactgttgccnccatgtattccagagttcttaaagtttaaagttgcacatgattg   84

REIC cDNA : 2526 tataagcatgctttctttgagttttaaattatgtataaacataagttgcatttagaaatc 2585
                 ||||||||||||||||||||||||||||||||||||||||||||||||||||||||||||
D11S2388  :   83 tataagcatgctttctttgagttttaaattatgtataaacataagttgcatttagaaatc   24

REIC cDNA : 2586 aagcataaatcacttcaactgct 2608
                 |||||||||||||||||||||||
D11S2388  :   23 aagcataaatcacttcaactgct    1
```

Non-small-cell lung cancers

Hepatocellular carcinomas

Colon cancers

Gastric cancers

Esophageal cancers

DECREASING CANCER CELL PROLIFERATION WITH WNT REMAINING ACTIVE

CROSS-REFERENCE TO RELATED APPLICATIONS

This application is a continuation of application Ser. No. 11/434,813, filed May 17, 2006, which is a divisional of application Ser. No. 10/130,360, accorded a filing date of Oct. 7, 2002, which is a U.S. National Phase PCT of International Application No. PCT/JP00/05879, filed Aug. 30, 2000, and which claims the benefit of foreign priority under 35 U.S.C. §119 based on Japanese Application No. 1999-330604, filed Nov. 19, 1999, the entire disclosures of which above-noted applications are hereby incorporated herein by reference, including any and all sequence listings, including those presented on paper and those presented in computer-readable format, e.g., copied onto diskette).

TECHNICAL FIELD

This invention relates to genetic information that can be useful in the treatment and diagnosis of diseases caused by the immortalization of cells such as cancer, as well as to its use. More specifically, the invention relates to genetic information than can express useful proteins for the treatment of diseases such as cancer which are expressed in immortal cells including cancer cells and which inhibit the proliferation of the cells, as well as to its use. Particularly, the invention relates to genes encoding the cell proliferation inhibitory proteins whose expression is reduced or disappeared in the immortal cells including cancer cells, as well as to their use for diagnostic agents or therapeutic agents.

BACKGROUND ART

Normal human cells are hardly immortalized and age. The normal human cells are destined to be aging according to the mechanism of counting the times of cell division (senescence mechanism). Ordinarily, the a living tissue gradually lose their proliferation capability and display aged morphology after having repeated subculturing (or division) 20 to 80 times. When a cell ages, it shows several morphological and biochemical changes, including cytomegalic tendency, squamous tendency, changes in extracellular matrix components, non-response to stimulation by mitogens and a decline in the expression function of proliferation regulating genes and it ceases to divide; therefore, it will be easy to be so judged.

However, when the cells are subjected to treatment with a carcinogen, or treatment by radiation during subculturing, a very small portion of the cells escape from this cell senescence and continue to grow, thereby forming a colony. The cells that have thus acquired the infinite proliferation capability (or that has experienced the failure of senescence mechanism) can be continuously cultured and do not die even after the passage of a finite number of cell generations: they are referred to as "immortal cells."

When a normal cell and an immortal cell are fused, the resulting hybrid cell displays finite division capability. Further, when immortal cells are fused with each other, there is obtained a hybrid cell displaying the finite division capability. This suggests that the immortalization is genetically recessive to senescence in human cells and that the deficiency of a particular gene (immortalization-suppressing gene) which is involved in the mechanism of counting the times of cell division (senescence mechanism) or the loss of its function is needed for cell immortalization.

Although it is not easy to directly prepare cancer cells from normal human cells, there is a close relation between the immortalization of cells and the cancerization of cells. It is beginning to be understood that in an experimental system where cells undergo cancerization under culturing conditions the normal human cells evade the senescence mechanism which strongly acts on their proliferation in a negative manner and mutate in a multistage such that the cells change into the immortalization stage allowing infinite proliferation and then into the cancerization stage with relative ease. For example, when the so-called oncogenes such as p53 mutant gene and Rb mutant gene are expressed in normal human cells, neither cancerization nor immortalization occurs; however, once the cells have been immortalized, they will easily turn cancerous by the oncogenes (Namba, M. et al., Crit. Rev. Oncogen., 7:19-31, 1996). This strongly suggests that the immortalization of cells is an important step in the cancerization of cells. Therefore, an analysis of the immortalization stage is critical to elucidating the carcinogenesis of human cells.

For proliferation inhibitory genes in cancer cells, there are mentioned more than ten kinds of genes, including Rb gene in retinoblastoma, p53 gene in colon cancer, and WT gene in Wilms tumor. Particularly, a preferred proliferation inhibitory gene is p53 and gene therapy using p53 has already begun (Li, H. et al., Clinical Cancer Res., 5, 637-642, 1999). Since immortalization of the cells is involved in the cancerization, not only cancer-suppressing genes but also the cell proliferation inhibition by the immortalization-suppressing genes will be effective treatment of cancer.

Thus far, there have been reported as genes associated with cell senescence and immortalization, Sdil (Noda, A. et al., Exp. Cell. Res., 211: 90-98, 1994), SEN6 (Banga, S. S. et al., Oncogene, 14: 313-321, 1997), SEN6A (Sandhu, A. K. et al., Oncogene, 12: 247-252, 1996), ING1 (Garkavtsev, I. and Riabowol, K., Mol. Cell. Biol., 17: 2014-2019, 1997), Hic-5 (Shibanuma, M. et al., Mol. Cell. Biol., 17: 1224-1235, 1997), among others. However, the correlation between these genes and the aging, immortalization, or cancerization of human cells has not been elucidated.

DISCLOSURE OF THE INVENTION

In view of the aforementioned circumstances this invention aims at identifying the complete lengths cDNA of an immortalization-suppressing genes and providing the information on said immortalization-suppressing gene and the function of proteins encoded by the genes.

As a result of having pursued diligent investigations to solve the above-stated problems, the present inventors isolated immortalization-suppressing genes encoding the proteins the expression of which is reduced or disappeared in the immortal cells including cancer cells, and identified plural nucleotides containing DNA sequences that corresponded to the translation region with 1050 bp (SEQ ID NO:2) encoding the protein having a 350 amino acid sequence (SEQ ID NO:1). They also found that the protein set forth in SEQ ID NO:1 in the Sequence Listing possessed cell proliferation inhibitory activity.

The present inventors further found that the immortalization-suppressing genes can be useful markers in the diagnosis of diseases such as cancer caused by the immortal cells and are genetic information capable of expressing proteins effective for the treatment of diseases such as cancer; and thus they completed this invention.

Specifically, this invention provides the proteins described in 1-2 below and polynucleotides:
1. A protein comprising an amino acid sequence derivable from the substitution or the deletion of one or more amino acids in the amino acid sequence set forth in SEQ ID NO:1 in the Sequence Listing, or from the addition of one or more amino acids to the amino acid sequence set forth in SEQ ID NO:1 in the Sequence Listing, said protein possessing cell proliferation inhibitory activity.
2. A polynucleotide comprising a DNA sequence derivable from the substitution or the deletion of one or more DNA in a DNA sequence selected from the group consisting of SEQ ID NO:2 in the Sequence Listing, SEQ ID NO:3 in the Sequence Listing, and SEQ ID NO:4 in the Sequence Listing, or from the addition of one or more DNA amino acids to a DNA sequence selected from the group consisting of SEQ ID NO:2, SEQ ID NO:3, and SEQ ID NO:4 in the Sequence Listing, said polynucleotide possessing cell proliferation inhibitory activity.

This invention also provides an antisense polynucleotide comprising an antisense DNA to a DNA comprising any one of DNA sequences described in 3-5 below, an antisense RNA to an RNA encoded by any one of DNA sequences described in 3-5 below, or a derivative of the foregoing:
3. A DNA sequence set forth in SEQ NO:2 in the Sequence Listing.
4. A DNA sequence set forth in SEQ NO:3 in the Sequence Listing.
5. A DNA sequence set forth in SEQ NO:4 in the Sequence Listing.

This invention also provides a cell proliferation inhibitory agent or a cancer therapeutic agent comprising a protein or a polynucleotide as described in 6-9 below:
6. A protein comprising the amino acid sequence set forth in SEQ ID NO:1 in the Sequence Listing.
7. A polynucleotide comprising the DNA sequence set forth in SEQ ID NO:2 in the Sequence Listing.
8. A polynucleotide comprising the DNA sequence set forth in SEQ ID NO:3 in the Sequence Listing.
9. A polynucleotide comprising the DNA sequence set forth in SEQ ID NO:4 in the Sequence Listing.

This invention also provides a cancer diagnostic agent characterized by using a protein as described in 1 or 6 above.

This invention also provides a cancer diagnostic agent characterized by using a polynucleotide as described in any of 7-9 above.

This invention further provides a composition for gene therapy comprising a polynucleotide as described in any of 7-9 above.

In the composition for gene therapy described above, the therapeutic gene is preferably contained in a viral vector; and more preferably, said viral vector is an Adenovirus vector.

Finally, this invention provides a method for differentiating a cancer cell comprising: providing a fluorescently-labeled antibody against a protein comprising the amino acid sequence set forth in SEQ ID NO:1 in the Sequence Listing; staining with the fluorescently-labeled antibody, a cell suspected of being a cancer cell; and determining the presence or absence of fluorescence emission.

BRIEF DESCRIPTION OF THE DRAWINGS

FIG. 1 is a diagram showing sequence alignment that represents a homology comparison between REIC (reduced expression in immortal cell) protein (SEQ ID NO: 1) used in this invention and hDkk3 protein or RIG7-1 protein (SEQ ID NO: 14).

FIG. 6 is a schematic representation showing the construction of a REIC/pGEX-2T expression plasmid used in this invention.

FIG. 7 is a representation corresponding to a photograph that shows the double-staining of KMS-6 cells by the immunofluorescence technique.

FIG. 10 is a diagram showing sequence alignment that represents homology comparison between the REIC gene SEQ ID NO: 15) according to this invention and the D11S2388 marker (SEQ ID NO: 16) shown in FIG. 9.

BEST MODE FOR CARRYING OUT THE INVENTION

Figure 2:
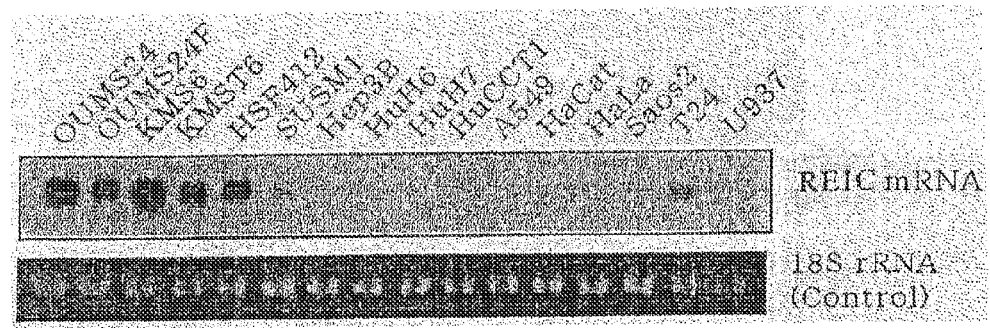
FIG. 2 is a representation corresponding to an autoradiograph showing the results of Northern blotting for the comparison of expression of REIC gene among a variety of human cell lines.

The constitution and preferred embodiments of this invention will be described in detail hereafter.

As used in this specification, amino acids, proteins, DNA sequences, nucleic acids, and the like are denoted in terms of various abbreviations according to the recommendations of IUPAC and IUB, "Guidelines for the Preparation of Specification Containing Base Sequences or Amino Acid Sequences" (Edited by the Japanese Patent Office), and conventional designations in the art to which this invention pertains.

As used in the specification, "polynucleotide(s)" may be embodied by a variety of forms such as single-stranded or double-stranded genomic DNA, cDNA, mRNA and cRNA.

In the specification, unless stated otherwise, DNA (including cDNA) refers to that comprising double strands, a sense strand and an antisense strand; and antisense DNA or antisense RNA refers to that comprising a single strand.

Further in the specification, the term "immortalization-suppressing" may be used in the same context as "cell proliferation inhibitory." Also, the term, "immortal cell(s)" is used to encompass cancer cell(s).

Also, the "antisense polynucleotide(s)" is encompassed by "polynucleotide(s)," but it is denoted "antisense polynucleotide(s)" when said polynucleotide is specifically stated to be an antisense strand.

(Immortalization-Suppressing Genes and Proteins)

One of the immortalization-suppressing genes used in this invention (which will be referred to as "gene(s) according to this invention" hereafter) is the isolated and purified polynucleotide (SEQ ID NO:2) comprising a DNA sequence encoding a protein comprising the 350 amino acid sequence set forth in SEQ ID NO:1 in the Sequence Listing, said protein possessing the cell proliferation inhibitory activity. The genes according to this invention also encompass a polynucleotide comprising the DNA sequence set forth in SEQ ID NO:3 or SEQ ID NO:4. The genes according to this invention further encompass a polynucleotide comprising a DNA sequence derivable from the substitution or the deletion of one or more DNA in any DNA sequence of the DNA sequence set forth in SEQ ID NO:2 in the Sequence Listing, the DNA sequence set forth in SEQ ID NO:3 in the Sequence Listing, and the DNA sequence set forth in SEQ ID NO:4 in the Sequence Listing, or from the addition of one or more DNA amino acids to any DNA sequence of the DNA sequence set forth in SEQ ID NO:2 in the Sequence Listing, the DNA sequence set forth in SEQ ID NO:3 in the Sequence Listing, and the DNA sequence set forth in SEQ ID NO:4 in the Sequence Listing.

When the protein comprising the amino acid sequence set forth in SEQ ID NO:1 is produced in vivo or in vitro and is to be utilized in this invention, it is not limited to the expression of a polynucleotide comprising the DNA sequence set forth in SEQ ID NO:2, SEQ ID NO:3 or SEQ ID:4. Any combination of codons corresponding to each amino acid constituting the aforementioned amino acid sequence may be used as the gene according to this invention to carry out the expression efficiently in a variety of hosts differing in the use frequency of codons. Accordingly, the scope of the genes according to this invention encompasses genes optionally containing such degenerate codons, other than the polynucleotides as defined above.

The cell proliferation inhibitory proteins used in this invention (which will be referred to as "protein(s) according to this invention hereafter) comprise a protein comprising the amino acid sequence set forth in SEQ ID NO:1; but they also encompass variants of said protein having amino acid sequences that have been modified from the amino acid sequence set forth in SEQ ID NO:1 by the substitution or the deletion of any one or more amino acids or by the addition of any one or more amino acids while retaining substantially the same cell proliferation inhibitory activity as has said protein. These variants typically include natural allelic variations and variations between animals of different species and have high homology to the amino acid sequence set forth in SEQ ID NO:1. In this invention the DNA sequences of polynucleotides may be altered correspondingly so that they should be able to encode the aforementioned variants. Desirable alterations of DNA sequences can be carried out by methods known to one skilled in the art such as site-specific mutation.

The protein consisting of the amino acid sequence set forth in SEQ ID NO:1 has been reported as hDkk3 protein which is a human homolog of Dkkl protein from *Xenopus* (Krupnik, V. E. et al., Gene 238, 301-313, 1999). XDkkl is a protein of the excretory type in the Spemann formation that has a potent head-inducing capability in the embryo of *Xenopus* and is involved in the differentiation of the embryo and the formation of the head part, and has been reported as a signal transduction-inhibiting factor for the Wnt family signaling molecules of the excretory type (Cadigan, K. M. and Nusse, R., Genes Dev. 11, 3286-3305, 1997). Krupnik et al. further have reported that although both hDkkl and hDkk4 have inhibitory activity against the Wnt activity of the signaling system for the Wnt family, hDkk3 does not have the inhibitory activity against the Wnt activity. The Wnt family proteins have been suggested to be cancer-related genes (Candigan, loc. cit.). However, the report by Krupnik et al. does not mention the correlation between hDkk3 and the Wnt family proteins. Therefore, prior to this invention there has been no information whatsoever that would suggest possible correlation between this hDkk3 protein and the immortalization or cancerization of cells.

For a molecule that is homologous to the protein comprising the amino acid sequence set forth in SEQ ID NO:1 or to the polynucleotide comprising the DNA sequence set forth in SEQ NO:2, RIG protein the expression of which is reduced in human glioma cells has been reported (Ligon, A. H., et al., J. Neuro Virology 4, 217-226, 1998). However, the RIG protein has low homology to the protein comprising the amino acid sequence set forth in SEQ ID NO:1 and thus differs from the latter protein according to this invention with respect to both function and structure.

(Expression of the Immortalization-Suppressing Genes in Various Cell Lines)

It is anticipated that the genes according to this invention, being immortalization-suppressing genes, are expressed in various human cells. When its expression in various human cancer cells and immortal cells was studied, it was found that the expression was disappeared in nine human cancer cell lines and one human immortal cell line and the expression was reduced in three human immortal cell lines, out of 10 human cancer cell lines obtained from various tissues such as lung cancer, hepatoma, lymphoma, and osteosarcoma. Furthermore, when the gene according to this invention was forced to express in a human immortal cell, the proliferation of this cell was found to be significantly inhibited. Accordingly, the genes according to this invention have the proliferation inhibitory activity against these cells.

(Chromosomal Mapping)

When the chromosomal mapping of the gene according to this invention was conducted, it was found that the gene could be mapped on human chromosome 11 short arm 15 (11p15). In the 11p15 region there have been reported the following genes or the genes that cause the following diseases to be present: Beckwith-Wiedemann syndrome, dopamine receptor D4, hemoglobin β-globin chain, drepanocytosis, cdk inhibitor p57$^{kip2}$, H-ras, IGF-II, insulin, QT elongation syndrome, adrenal cortex cancer, Wilms tumor 2, rhabdomyosarcoma, lactic acid dehydrogenase, Niemann Pick cell disease, adrenal cortex thyroid gland hormones, and Usher's syndrome. The instability of chromosome at 11p15 has been reported in various solid cancers such as non-small-cell lung cancer, hepatoma, gastric cancer, esophageal cancer, head and neck cancer, prostate cancer, and ovarian cancer (Lalande, M., Annu. Rev. Genet., 30, 173, 1997; Freinberg, A. P., Cancer Res., 59, 1743-1746, 1999). Further in the experiment where human chromosomal DNA is introduced into cell lines derived from pulmonary adenomatosis and rhabdomyoma, cancer-suppressing genes have been reported to be mapped on 11p15 (O'Briant, K., et al., Anticancer Res., 17, 3243-3251, 1997; Reid, L. H., et al., Hum. Mol. Genet., 5, 239-247, 1996). These reports suggest the possibility that the instability of chromosomes such as the loss of heterozygosity (LOH) and genome-imprinting brings the reduced expression of the genes according to this invention and it causes cell cancerization to be induced. Further, it is strongly suggested that said genes are not only cell immortalization-suppressing genes, but also cancer-suppressing genes.

(Availability of the Immortalization-Suppressing Genes)

The genes according to this invention can be obtained based on the DNA sequence information disclosed by this specification following gene manipulation techniques (for example, Molecular Cloning 2nd ed., Cold Spring Harbor Laboratory Press: 1989).

In practice, the genes according to this invention can be obtained by concentrating and selecting cDNA of genes that are expressed in normal cells in a high degree but in immortal cells in a low degree according to Represetational Difference Analysis (RDA), as will be shown in the examples. Furthermore, the full-length cDNA of the gene can also be selectively obtained from a long-strand cDNA library prepared by size fractionation, the oligo-capping method or the Race method. Specifically, KMS-6 cells, which were aged normal cells, and KMST-6 cells, which were immortal cells, could produce a novel cDNA with at least 266 bp showing reduced expression in the immortal cells through the RDA method. By employing similar treatment, it is possible to obtain homologs encompassed by the genes according to this invention from the materials of various immortal cells and the normal cells which are their parent cell line. One skilled in the art can readily select the cell lines required as the materials.

DNA sequence of the thus obtained gene is based to prepare a specific probe with an arbitrary sequence and length; the probe can be used to screen a human heart cDNA library by colony hybridization, plaque hybridization, or the like, and cDNA containing an immortalization-suppressing gene can be isolated. Similar screening can also be carried out on a human heart cDNA library prepared by the oligo-capping method and cDNA containing an immortalization-suppressing gene can be isolated.

Furthermore, the desired cDNA clones can be isolated from various human cDNA libraries that are commercially available or from cDNA libraries prepared from various cultured cells and tissues according to conventional methods. By using an amino acid sequence corresponding to the DNA sequence of the aforementioned gene and antibodies specific thereto, the desired cDNA clones can also be selected according to immunological screening methods. In addition, specific PCR primers are designed based on the DNA sequence of the gene fragment described above as appropriate. PCR can then be carried out following a conventional method to select the desired cDNA clones retaining the amplified DNA fragment from the cDNA library.

(Gene Expression Systems)

When the gene according to this invention is to be utilized, preferably a polynucleotide at least containing the DNA sequence set forth in SEQ ID NO:2 in the Sequence Listing or a DNA sequence consensus thereto is incorporated into a suitable expression cassette and/or an suitable expression vector and the protein comprising the amino acid sequence set forth in SEQ ID No:1 or a variant thereof is expressed in a targeted human cell.

As for the expression cassettes, any cassettes without any particular limitations may be used insofar as they can allow genes according to this invention to express in the target cells. One skilled in the art can readily select such expression cassettes. Preferably, they are expression cassettes capable of gene expression in the cells derived from an animal, more preferably, expression cassettes capable of gene expression in the cells derived from a mammal, and most preferably expression cassettes capable of gene expression in the cells derived from a human.

The expression cassette can employ, in addition to the gene according to this invention, any sequence among a promoter or enhancer for the transcription of the gene, a poly-A signal, a marker gene for labeling and/or selecting the cell into which the gene has been introduced, a virus-derived gene sequence for the efficient insertion of gene into cellular genomic DNA sequences, and a signal sequence for extracellularly secreting the substance that is produced by gene expression and that acts as drug and/or for having the substance remained at localized sites within a cell.

The promoters that can be used in the expression cassettes include: for example, virus-derived promoters from Adenovirus (Ad), cytomegalovirus (CMV), human immunodeficiency virus (HIV), Adeno-associated virus (AAV), simian virus 40 (SV40), Rous sarcoma virus (RSV), herpes simplex virus (HSV), murine leukemia virus (MoMLV), Sinbis virus, Sendai virus (Sev), hepatitis type A virus (HAV), hepatitis type B virus (HBV), hepatitis type C virus (HCV), papilloma virus (HPV), human T cell leukemia virus (HTLV), vesicular stomatitis virus, influenza virus, Japanese encephalitis virus, JC virus, parbovirus B19, poliovirus, and the like; mammal-derived promoters such as α-subunit of the signal recognition particle receptor (SR-α), myelin basic protein (MBP), glial-specific glial fibrillary acidic protein (EF1-α), glyceraldehyde-3-phosphate dehydrogenase (GAPDH), multidrug resistance gene (Mdrl), albumin α-fetoprotein (AFP), heat shock protein (HSP), hypoxia-inducing protein (HIP); and chimera type promoters such as a chimera promoter (CAG) comprising a CMV initial phase enhancer/chicken β-actin promoter/β-globinpolyA, and a chimera promoter comprising a CMV initial phase enhancer/α-skeletal actin promoter.

Also, there may be used a gene and LTR to form LTR of the chimera type wherein the U3 region of LTR has been replaced by a promoter such as CAG, CMV, RSV, TK, SV40, SR-α, MBP, β-actin, or EF1-α: LTR is a promoter derived from a retrovirus capable of expressing the gene.

The expression cassette containing the gene according to this invention can be incorporated into a cosmid, a plasmid, or any virus-derived recombinant vector that is compatible with a host cell. There are no limitations to the kind, the molecular weight, the form, or the like of such a recombinant viral vector. Specifically, there are mentioned DNA and/or RNA viruses, and (+) and/or (−) chains, but no particular limitations should be imposed.

The recombinant viral vectors may be any viral vector of MoMLV vector, HSV vector, Adenovirus vector, AAV vector, HIV vector, Sev vector and the like. One or more proteins among the constituent protein group of a viral vector are substituted by the constituent proteins of a different species of virus, or alternatively a part of the nucleic acid sequence constituting genetic information is substituted by the nucleic acid sequence of a different species of virus to form a viral vector of the pseudo-type, which can be used in this invention. Further, viruses having a host spectrum other than human are usable as the recombinant viral vector insofar as they will be efficacious.

As described in detail above, the gene according to this invention can be incorporated into an expression vector of a microorganism or eucaryote that serves as a host cell to produce a transformed microorganism or eucaryote, from which the protein comprising the amino acid sequence set forth in SEQ ID NO:1 can be produced easily and stably by culturing. The expression vector selected among the named ones above alone, or after forming a complex with a variety of medically acceptable carriers such as cationic polymers, polylysine, and polylysine-serine, can be introduced into host cells.

(Antisense Polynucleotides)

For the sense strand of DNA constituting the gene according to this invention and RNA encoded by the DNA, antisense DNA and antisense RNA exist respectively each of which comprises a base sequence complementary to the base sequence of the foregoing DNA or RNA. Specifically, such antisense DNA has a DNA sequence that is complementary to at least part of the DNA sequence set forth in SEQ ID NO:2, SEQ ID NO:3, or SEQ ID NO:4. Also, such antisense RNA has a RNA sequence that is complementary to at least part of RNA encoded by DNA comprising the DNA sequence set forth in SEQ ID NO:2, SEQ ID NO:3, or SEQ ID NO:4. Preferably, the antisense DNA or the antisense RNA is complementary to part of the DNA sequence set forth in SEQ ID NO:2 or to part of the corresponding RNA sequence. Therefore, the antisense polynucleotide comprising the DNA or the RNA hybridizes to the DNA or the RNA that carries genetic information during the process of production of the protein according to this invention from the gene according to the invention (transcription, translation and etc.), and affects the normal flow of transmission of the genetic information, thus inhibiting the biosynthesis of said protein. This invention also encompasses antisense derivatives. For example, the derivative is one wherein a different substance is attached to the 3'- or the 5'-end of the antisense nucleotide, or one wherein at least part of the bases, sugars, or phosphates is modified by substitution, deletion or addition. Especially, when considering administration to the living body, preferred is a polynucleotide derivative of the phosphothioate type (a phosphate group is covalently bonded by sulfur atom) so that decomposition by nuclease can be prevented. It is preferred that the antisense polynucleotide or a derivative thereof have a base number of from 10 to 2,000. Within this range, oligonucleotides having a relatively small base number can be synthesized chemically using a DNA synthesizer. Further, it is sometimes possible that part of cDNA of the gene according to this invention is used as a template to attain the synthesis by PCR.

(Utility as Therapeutic Agents)

Because the proteins according to this invention inhibit the proliferation of immortal cells including cancer cells, they can be used as therapeutic agents in the treatment of diseases (e.g., cancer) caused by the immortalization of the cells. Therefore, the genes according to this invention encoding these proteins are also usable as therapeutic agents. In addition, the antisense polynucleotides of this invention or derivatives thereof act on the genes according to this invention in an antagonistic manner and stimulate the cell proliferation; therefore, they are applicable to the treatment of various disorders.

When the protein according to this invention is to be used as a cell proliferation inhibitory agent or a cancer therapeutic agent in the treatment of diseases such as cancer, the protein is preferably administered to a patient as a tablet, capsule, injectable suspension, or other formulation together with a pharmaceutically acceptable carrier, diluent, excipient, stabilizer, or the like. The auxiliary agents used for this purpose are well known to one skilled in the art. When the desired route of administration is set such as intravenous administration or oral administration, the cell proliferation inhibitory agents and the cancer therapeutic agents of this invention can be expected to accomplish desired therapeutic effects.

(Application in Gene Therapy)

When the gene according to this invention is used as the cell proliferation inhibitory agent or as the cancer therapeutic agent in the treatment of diseases such as cancer, preferably said gene as the therapeutic gene is combined with the carrier designed for the therapy to prepare a composition for gene therapy, which is administered to a patient.

The composition for gene therapy of this invention can be used in the gene therapy through autologous implantation (ex vivo gene therapy) where the target cells are first removed outside the body from a patient and the cells are then returned to the body of the patient after the gene according to this invention has been transferred into the cells. The gene according to this invention can also be used in the gene therapy where the therapeutic gene is directly administered to the patient (in vivo gene therapy).

When the gene according to this invention is used in the gene therapy, an Adenovirus vector is preferably used. The characteristics of the Adenovirus vector include the following: (1) it can transfer genes into many kinds of cells; (2) it can efficiently transfer genes into even cells at their growth arrest phase; (3) concentration through centrifugation can be done to produce virus with high titer (10 to 11 PFU/ml or more); and (4) it is suitable for direct gene transfer into tissue cells in vivo.

With regard to Adenovirus for gene therapy, there have been developed the first generation Adenovirus vector where the E1/E3 region is deleted (Miyake S., et al., Proc. Natl. Acad. Sci. USA., 93, 1320, 1996), the second generation Adenovirus vector where the E2 or the E4 region in addition to the E1/E3 region is deleted (Lieber, A., et al., J. Virol., 70, 8944, 1966; Mizuguchi, H. & Kay, M. A., Hum. Gene Ther., 10, 2013, 1999), the third generation Adenovirus vector where the Adenovirus genome is almost completely deleted (GUTLESS) (Steinwaerder, D. S., et al., J. Virol., 73, 9303, 1999). Any Adenovirus vector is usable without particular limitations when the gene according to this invention is subjected to gene transfer.

Furthermore, application in the long term gene expression is possible by utilizing an Adeno-AA hybrid vector where AAV's chromosome is provided with the incorporation capability (Recchia, A., et al., Proc. Natl. Acad. Sci., USA., 96, 2615, 1999), or an Adenovirus vector which has acquired the chromosomal incorporation capability through the use of the gene of transposon.

It is also possible to provide an Adenovirus vector with tissue specificity by inserting into the H1 loop of the Adenovirus fiber, a peptide sequence displaying tissue-specific migration (Mizuguchi, H. & Hayakawa, T., N. Nippon Rinsho, 7, 1544, 2000).

Methods for administering the composition for gene therapy of this invention to the living body are not particularly limited. They may preferably be carried out by, for example, parental administration such as intravenous administration.
(Objective Disorders)

The protein according to this invention encoded by the gene according to the invention induces the aged state or the quiescent state of a recipient cell; therefore, it can mediate the differentiation of a cancer cell into a non-cancerous cell. For example, it can be used in the treatment to inhibit the rapid proliferation of cancer cells or original cancer cells.

Generally, there are benign tumor and malignant tumor in "tumor," the latter of which is collectively referred to as "cancer."

The tumors that can be treated by the proteins according to this invention are not particularly limited; and they can be used to treat both of the benign tumors and the malignant tumors, and are especially effective for the malignant tumors.

When malignant tumors are classified according to the organs from which they have developed, the classification is as follows: brain and nerve tumor, skin cancer, gastric cancer, lung cancer, hepatoma, lymphoma, leukemia, colon cancer, pancreatic cancer, anal and rectal cancer, esophageal cancer, uterus cancer, breast cancer, osteoma/osteosarcoma, leiomyoma, rhabdomyoma, and other cancers. As stated above, the tumors that can be treated are not particularly limited and any of the aforementioned tumors and cancers can be treated; treatment is effective against lung cancer, hepatoma, esophageal cancer, and osteoma/osteosarcoma.

When the cancers of the respective organs are further classified histologically, they are largely classified into carcinomas derived from epithelial cells, sarcomas derived from non-epithelial cells and the mixed tumors of the two. The tumors that can be treated by the proteins according to this invention are not particularly limited; and they can be used to treat any of the carcinomas derived from epithelial cells, the sarcomas derived from non-epithelial cells and the mixed tumors, and are especially effective for the carcinomas derived from epithelial cells.

In addition, many non-cancerous diseases can be treated by the proteins and the genes according to this invention, and their representatives include disorders caused by the hyperplasia of cells such as glaucoma and psoriasis.

Retrovirus proliferates only in the cells at their growth phase; therefore, the genes according to this invention are expected to be therapeutically effective against diseases such as retrovirus infections (e.g., HIV), warts (including venereal wart), papilloma (?), and progressive multifocalleucocephalopathy. This is because the genes suppress the proliferation of the virus by inhibiting the proliferation of the infected cells. Consequently, they find utility as antiviral agents in suppressing the proliferation of viruses such as influenza virus, hepatitis virus (e.g., hepatitis A and hepatitis B), EBV (Epstein-Barr virus), and papilloma virus.

Since the antisense polynucleotides or their derivatives of this invention posses the activity of stimulating cell proliferation, they can be used in the treatment of disorders requiring the cell proliferation. For example, there are mentioned the proliferation of dermal tissue cells for the purpose of treating wounds, burns and the like, the proliferation of angioendothelial cells for the purpose of treating myocardial infarction, cerebral infarction and the like, the proliferation of atrophic tissue cells for the purpose of treating cirrhosis, renal insufficiency and the like, the proliferation of marrow cells for the purpose of treating the decreased lymphocytes resulting from radiation exposure, AIDS and the like.
(Utility as Therapeutic Agents)

As stated above, the genes according to this invention can be diagnostic markers broadly for diseases caused by the proliferation of immortal cells because their expression is reduced in the immortal cells, including cancer cells. Particularly, the genes according to this invention are usable as cancer diagnostic agents. Further, the proteins according to this invention expressed by the genes according to the invention also experience their reduced expression in the immortal cells, including cancer cells; therefore, they can be used as the diagnostic markers inclusive of the cancer diagnostic agents similarly.

When the protein according to this invention is used in the diagnosis of cancer among others, antibodies specific for the protein are prepared and used in assays. Here, the protein or a part thereof may be used that is produced in a large quantity according to the aforementioned gene manipulation techniques. The obtained antibodies may be either polyclonal antibodies or monoclonal antibodies. These antibodies may be utilized in the purification, the measurement, and the identification of the protein. In particular, the monoclonal antibodies can preferably be used in immunoassays for evaluating the presence of the protein in cells, tissues, or body fluids. Thus, the capabilities provided by the antibodies to detect and/or measure the proteins are very desirable as evaluation means for the presence of tumors or the degree of their severity.
(Gene Diagnosis)

When the gene according to this invention is used in the gene diagnosis for cancer among others, a polynucleotide is prepared and used in an assay: the polynucleotide is based on the DNA sequence constituting the gene which polynucleotide contains DNA hybridizable to said DNA sequence or RNA hybridizable to the RNA sequence corresponding to said DNA sequence. For this purpose, the full-length or part of the antisense polynucleotide described above may be used. The length of such a polynucleotide is preferably from 10 to 2,000 bases, and more preferably from 15 to 1,000 bases. This polynucleotide may be adequately labeled with a radioisotope such as $^{32}P$, an enzyme such as alkaline phosphatase, a fluorescent compound such as fluorescein, or a chemiluminiscent compound such as acrynidium ester. The resulting labeled polynucleotides can be used as DNA and/or RNA probes in assays, including conventional analyses such as Southern or Northern blotting. Preferably, these probes can be hybridized to the aforementioned genes under stringent conditions. The short polynucleotides with 10 to 50 bases may also be used as primers in the diagnosis by PCR.

EXAMPLES

This invention will be described more concretely by way of examples; however, the invention is not to be limited by these examples.

Example 1

Cloning Immortalization-Related Genes

1. Culturing the First Generation Fibroblast Line

Human fibroblasts were prepared from a female embryo of 9 weeks old to form the first generation fibroblast line (KMS-6) (Namba, M. et al., Int. J. Cancer, 35: 275-280, 1985). The cells were cultured with an Eagle minimum medium (MEM available from GIBCO) containing 10% fetal bovine serum (FBS available from Sanko Pure Chemicals Co. Ltd.) or with a Dalbeco modified Eagle medium (DMEM available from GIBCO) under the conditions of 5% $CO_2$ concentration and 37° C. After the cells were grown until almost confluent state in a plate for 5 to 7 days, cells were diluted ¼-fold and subcultured.

2. Establishing an Immortal Cell Line by Treatment with $^{60}Co$ Radiation

KMS-6 cells that had been cultured semiconfluent were radiated with $^{60}Co$ γ-ray having a dose of from 200 to 400 rads 13 times and were subjected to radiation treatment with a total of 2,800 rads. Subsequently, subculturing was repeated at ½-fold per time and about 50 times of subculturing was conducted in total. The immortal cell line (KMST-6) was obtained that displayed no aged morphology and had proliferation capability (Namba et al., loc. cit).

3. Cloning Genes by RDA

Total RNA was extracted from KMS-6 cells that had been aged by subculturing through 45 passages according to the Acid-Guanidium-Phenol-Chloroform (AGPC) method and mRNA was purified with Dyna beads (Dynal Inc.). In like manner, mRNA was extracted and purified from the immortal KMST-6 cells. Each 2 μg of the purified mRNAs was used as a template to prepare the respective cDNAs, by employing avian myeloblastosis virus reverse transcriptase (AMV-RT). cDNA prepared from KMS-6 (0.01 μg) and cDNA prepared from KMST-6 (1 μg) were subjected to subtraction at 68° C. for 8 hours. cDNA that had not been removed through subtraction was used as a template to prepare a double-stranded DNA, by employing T4DNA polymerase. This was incorporated into a pT7Blue (Novagen) plasmid vector and then, it was introduced into E. coli (DH5 α) to produce an E. coli library comprising about 400 clones.

Example 2

REIC Clone

1. Screening the E. coli Library

To remove pseudo-positive clones from the E. coli library, $^{32}P$ labeled cDNA probe was prepared based on mRNA of OUMS-24F, a different immortal cell line (Bai, L. et al., Int. J. Cancer, 53: 451-456, 1993); the probe was used to carry out colony hybridization. The hybridization resulted in the removal of clones that had proved positive and the production of about 30 immortal candidate clones.

2. DNA Sequencing

The DNA sequences of the clones obtained by screening were determined according to the Sanger method (Sanger F. et al., Proc. Natl. Acad. Sci. USA 74: 5463-5467, 1977). Consequently, clones were identified that had the aging-related gene sequences, including fibronectin, extracellular matrix proteins (e.g., α2 type I procollagen), collagenase, enzyme proteins (e.g., WS9-14), cell cycle regulating proteins (e.g., p21). Among these, it was found that REIC clone (D93) displaying no homology to known genes and being regarded as a novel gene had been obtained. The DNA sequence is shown in SEQ ID NO:5 in the Sequence Listing.

Example 3

REIC Clone (10-1)

The DNA sequence of REIC clone (D93) predicted that the clone was not of the complete length cDNA. The polynucleotide having the DNA sequence set forth in SEQ ID NO:5 was used as a probe to screen a human heart cDNA library (BRL Inc.) for clones having cDNA fragments with longer DNA sequences. Consequently, there was obtained an REIC clone (10-1) that was predicted to carry the full-length cDNA containing the 5'-region of REIC (D93). DNA sequencing was conducted on this cDNA clone and the entire DNA sequence was determined. The DNA sequence of this clone is shown in SEQ ID NO:3 in the Sequence Listing.

Example 4

REIC Clone (10-2)

Human heart cDNA library (Nippon Gene Co. Ltd.) prepared according to the oligo capping method (Maruyama, K. and Sugano, S., Gene, 138: 171-174, 1994) was employed. Similarly to Example 2, the polynucleotide having the DNA sequence set forth in SEQ ID NO:5 was used as a probe to screen the library for clones having cDNA fragments with longer DNA sequences. Consequently, there was obtained a REIC (10-2) clone that was predicted to carry the full-length cDNA containing the 5'-region of REIC (D93). DNA sequencing was conducted on this cDNA clone and the entire DNA sequence was determined. The DNA sequence of this clone is shown in SEQ ID NO:4 in the Sequence Listing.

Example 5

Analysis of Cloned cDNA

The results from Examples 3 and 5 confirmed that the gene according to this invention completely contained the DNA sequence set forth in SEQ ID NO:5 (which corresponds to base nos. 1848 to 2113 in SEQ ID NO:3 and to base nos. 1820 to 2095 in SEQ ID NO:4, respectively) in addition to the translation region of 1050 bp (which corresponds to base nos. 226 to 1275 in SEQ ID NO:3 and to base nos. 198 to 1247 in SEQ ID NO:4, respectively) set forth in SEQ ID NO:2 encoding the protein having 350 amino acids (SEQ ID NO:1) at the 5'-end side of the foregoing DNA sequence. As previously mentioned, this gene is represented as "Reduced Expression in Immortal Cell (REIC))" and will be referred to as "REIC gene" or simply "REIC," because its expression is reduced in the immortal cells.

A search for any homologs to the REIC gene according to this invention was carried out in the database disclosed on the Web site by NCBI (National Center for Biotechnology) using a homology analysis program (BLAST).

The result of BLAST produced hDkk3 and RIG7-1 that were identical or homologous to the amino acid sequence set forth in SEQ ID NO:1. hDkk3 displayed 100% identity, while RIG7-1 was partially identical and displayed only 43% homology as a whole. A homology comparison between the amino acid sequences for hDkk3 and RIG7-1 and the amino acid sequence of REIC gene (SEQ ID NO:1) is shown in FIG. 1.

Example 6

Analysis of the Expressed Amounts of REIC in Various Cell Lines

Total RNAs were prepared from 11 kinds of cancer cell lines, Hep3B (hepatocellular carcinoma), HuH6 (congenital hepatoma), HuH7 (hepatocellular carcinoma), HuCCT1 (cholangioma), A549 (lung cancer), HaCat (immortal keratinocyte), HeLa (carcinoma of uterine cervix), Saos2 (osteosarcoma), T24 (bladder cancer), and U937 (histiocytic lymphoma), three kinds of normal fibroblasts, OUMS24, KMS-6, and HSF412, and their corresponding immortal cell lines, OUMS24F, KMST-6, and SUSM1, respectively. The total RNA (10 µg) was electrophoresed on 1% formaldehyde/agarose gel and fixed on a nitrocellulose film (Hybribond N+ available from Amersham Pharmacia Biotech Inc.). Next, a probe labeled with ($\alpha$-$^{32}$P)-dCTP was used to carry out Northern hybridization of the REIC cDNA fragment (at 42° C. for 12 hours). The membrane was placed in a buffer containing 5×SSC, 50% formamide, 1×Denhart solution, 0.2% SDS, 19% dextran sulfate, and thermally denatured salmon sperm DNA (200 µg/ml); and to this was added probe DNA labeled with a radioisotope and hybridized at 65° C. Subsequently, the filter was washed in 2×SSC/0.5% SDS buffer at 55° C. and in 0.1×SSC/0.5% SDS buffer at 55° C. once more. The result obtained from autoradiography on an X-ray film is shown in FIG. 2. mRNA the size of which was about 2.6 kb was detected in the normal cell lines. It was shown that the size of this transcript was consistent with the size of the DNA sequence for REIC cDNA as set forth in SEQ ID NO:3 or SEQ ID NO:4. Although the expression of the REIC gene was noted in each of the immortal cell lines, its expression amount was reduced as compared to the normal cell lines. Further, the disappearance of expression of the REIC gene was confirmed in each of the cancer cell lines, except for T24 cell line.

Example 7

Cell Proliferation Inhibition Test

Figure 3:
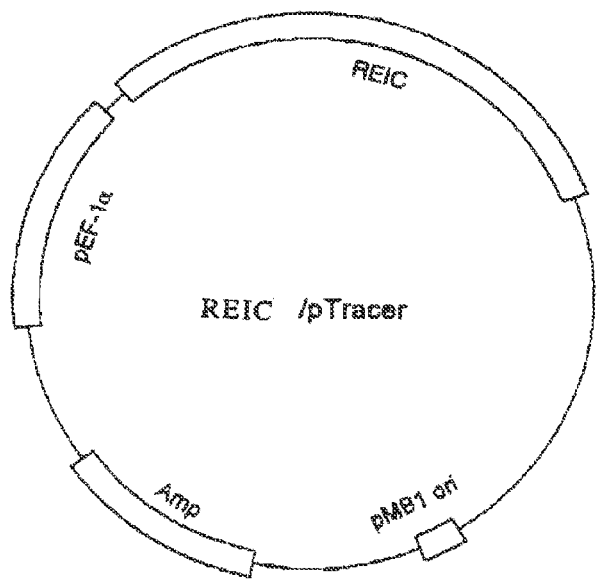
FIG. 3 is a schematic representation showing the construction of a REIC/pTracer expression plasmid used in this invention.
Figure 4:
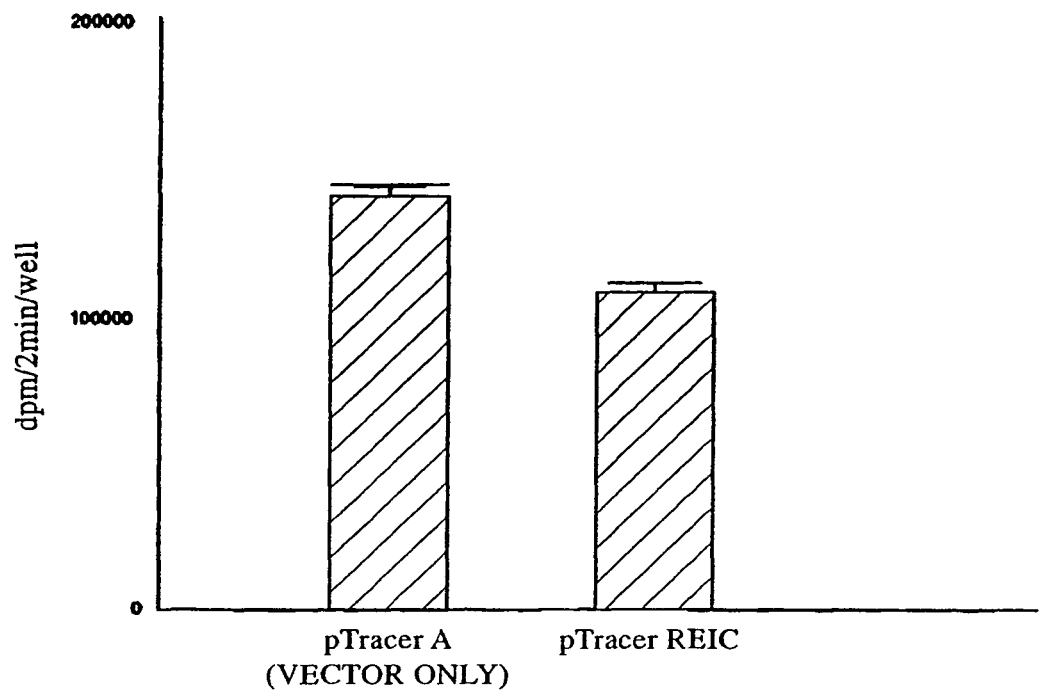
FIG. 4 is a graph showing the test results of $^3$H thymidine incorporation into immortal KMST-6 cells according to this invention.
Figure 5:
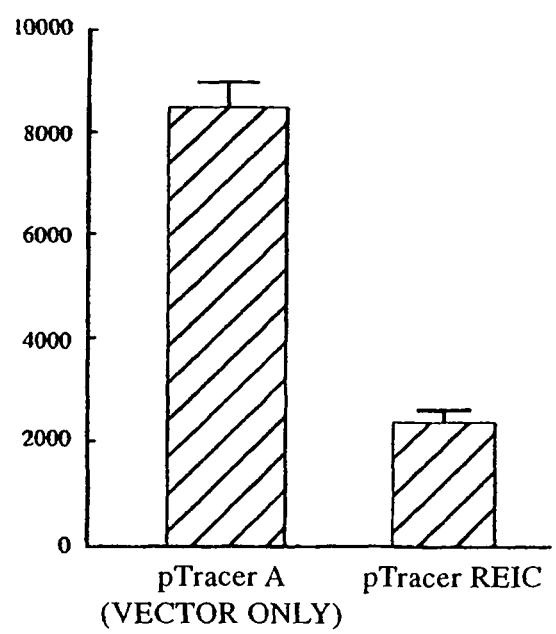
FIG. 5 is a graph showing the test results of $^3$H thymidine incorporation into Saos2 osteosarcoma cells according to this invention.

1. Preparation of an Expression Plasmid
Plasmid vector pTracer A (Invitrogen) carrying EF-1$\alpha$ was employed as a gene expression promoter. A 2.6 kb-REIC cDNA fragment that had been cut out with EcoRI-XbaI and contained the DNA sequence set forth in SEQ ID NO:3 was subcloned into the EcoRI-XbaI site in the downstream of the EF-1$\alpha$ promoter to produce an REIC/pTracer expression plasmid (FIG. 3).
2. Incorporation of $^3$H Thymidine (Immortal KMST-6 Cells)
Immortal KMST-6 cells were inoculated on a 24-well plate at 2×10$^4$ cell/well. Lipofectamin (GIBCO Inc.) was used as a transfection reagent to carry out the lipofection of 5 µg of REIC/pTracer expression plasmid. Methyl-3H thymidine (1 Ci/mmol) was prepared at a level of 1 µCi/well and cell incorporation was conducted. The obtained cells were washed with chilled PBS(−) after 12 hours. Further, the cells were fixed in 5% trichloroacetic acid and washed with 95% ethanol. After the thus obtained cells were dissolved in 0.3 M NaOH, the cells were neutralized with HCl and the radioactivity of the incorporated $^3$H thymidine was measured with a liquid scintillation counter. Consequently, the REIC gene was confirmed to posses cell proliferation inhibition effect (FIG. 4). As a control, only the pTracerA vector was subjected to lipofection into the KMST-6 cells.
3. Incorporation of $^3$H Thymidine (Saos2 Osteosarcoma Cells)
Saos2 osteosarcoma cells were inoculated on a 24-well plate at 5×10$^4$ cell/well. The calcium phosphate method was used to carry out the transfection of 2 µg of the REIC/pTracer expression plasmid. Methyl-3H thymidine (1 Ci/mmol) was prepared at a level of 1 µCi/well and cell incorporation was conducted. The cells were washed with chilled PBS(−) after 12 hours. Further, the cells were fixed in 5% trichloroacetic acid and washed with 95% ethanol. After the thus obtained cells were dissolved in 0.3 M NaOH, the cells were neutralized with HCl and the radioactivity of the incorporated $^3$H thymidine was measured with a liquid scintillation counter. Consequently, the REIC gene was confirmed to posses cell proliferation inhibition effect (FIG. 5). As a control, only the pTracerA vector was subjected to lipofection into the Saos2 cells.

Example 8

Preparation of Antibodies Recognizing REIC Protein

1. In Vitro Translation of REIC Protein
The REIC protein was translated in an in vitro expression system to have it expressed as a GST fusion protein.
Based on the DNA sequence set forth in SEQ ID NO:3, primers, 5'-TGGATCCATGCAGCGGCTTGGGGCCAC-3' (SEQ ID NO:6) and 5'-TGAATTCAATCTCTTCCCCTC-CCAGCAG-3' (SEQ ID NO:7) were used to selectively amplify the ORF region of REIC. The amplified DNA fragment was digested with BamHI and EcoRI and subcloned into the BamHI-EcoRI site of pGEX-2T, a GST fusion protein expression plasmid (Amersham Pharmacia Biotech) so that REIC could be expressed as a fusion protein, producing a REIC/pGEX-2T expression plasmid (FIG. 6).
E. coli transformed with the REIC/pGEX-2T plasmid was subjected to IPTG induction treatment according to a conventional method, whereby the fusion protein was produced. The harvested E. coli cells were suspended in PBS and subjected to ultrasonic treatment. Then, the supernatant obtained from centrifugation was charged onto a glutathione Cephalose 4B column (Amercham•Pharmacia Biotech Inc.) and the fusion protein was purified. The fusion protein adsorbed on the column was digested with thrombin and eluted.
Subsequently, the fusion protein that had not been digested was removed through a glutathione column again and the REIC protein having a few extra amino acids was obtained.
2. Antibodies
The protein that had been obtained in Example 1 above and purified was diluted with physiological saline solution and 1 mg was administered a rabbit in an otic vein thereof every two weeks to immunize the animal. After twice immunization, the antibody titer was measured using an ECL Western blotting (Amersham Pharmacia Biotech Inc.). Consequently, it was confirmed that the antibodies diluted 2000-fold were reactive to 0.01 µg of the protein. Thus boostering was conducted twice. The blood obtained by whole blood collection was incubated at 37° C. for 30 minutes. After the coagulated blood clot was removed, the blood filtered in a sterilized condition using a filter with a pore size of 45 µm to produce the desired antiserum.

Example 9

Antibody Staining of Cell Nuclei

To examine the intracellular localization of the REIC gene, cells were subjected to double staining by using the anti-REIC antiserum prepared in Example 8 and Hoechst33258 (Molecular Probe Inc.) as the control which was a dye capable of fluorescently staining chromosomes specifically. KMS-6 cells were first cultured in a 6-well Petri dish. Hoechst33258 was added to a medium to give a level of 100 ng/ml and culturing was done for 1 hour. The cells stained with Hoechst33258 were fixed in 1% paraformaldehyde and after treatment with the antiserum described above, the cells were stained with a FITC-labeled goat-anti-rabbit antibody (Sigma Inc.). While Hoechst33258 was excited at 360 nm wavelength, the FITC-labeled antibody was excited at 488 nm wavelength. The results of measurement according to this immunofluorescence technique are shown in FIG. 7. This confirmed that the antiserum specifically stained the nuclei and the REIC protein was localized in the nucleus within the cell.

Example 10

Chromosomal Mapping of REIC Gene

Figure 8:
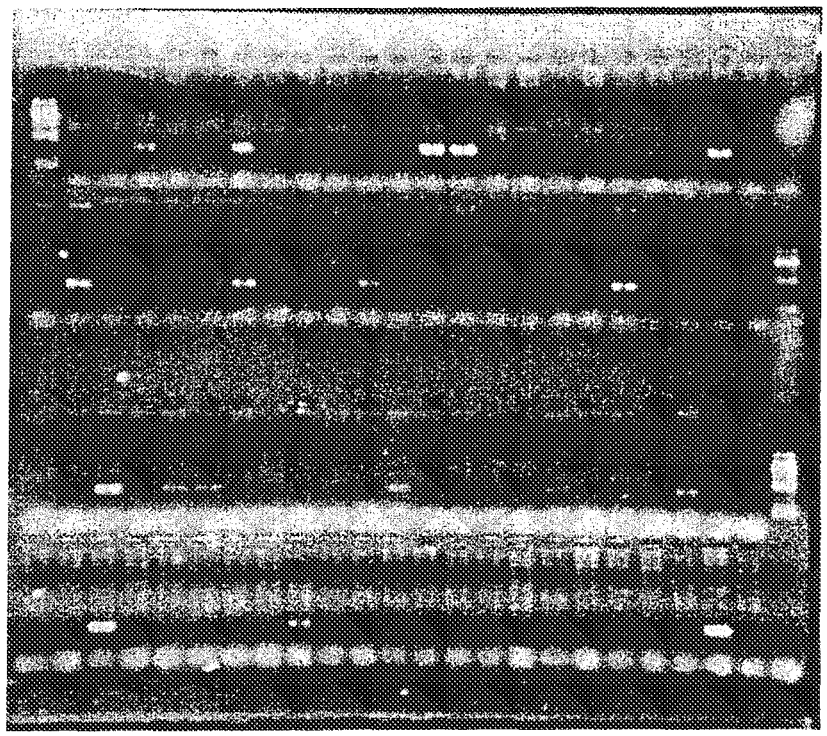
FIG. 8 is a representation corresponding to an electrophoresis photograph that shows a 553 bp amplified product obtained in Example 10.

The chromosomal map of the REIC gene was determined by using a panel derived from human-hamster hybrid cells (Standford G3 Human/Hamster RH Panel available from Research Genetics Inc.) and analyzing radiation-hybrid map (RH map). 5'-GATTTAGATCTGGACCAGGC-3' (SEQ ID NO:8) (base nos. 1244 to 1263 in SEQ ID NO:4) and 5'-CT-GAGCAACACTGCTGGATG-3' (SEQ ID NO:9) (antisense strand corresponding to base nos. 1777 to 1796 in SEQ ID NO:4) were used as PCR primers. After preheating at 94° C. for 3 minutes, 30-cycle reaction was carried out at 94° C. for 30 seconds, at 63° C. for 30 seconds, and at 72° C. for 1 minute in PCR. After subjecting the reaction solution to electrophoresis on 2% agarose gel, staining with ethidium bromide (EtBr) resulted in the confirmation of a 553 bp amplified product (FIG. 8). The result of PCR identified from the RH database at Stanford University that the REIC gene was located at human chromosome 11 short arm 15 (11p15).

Figure 9:
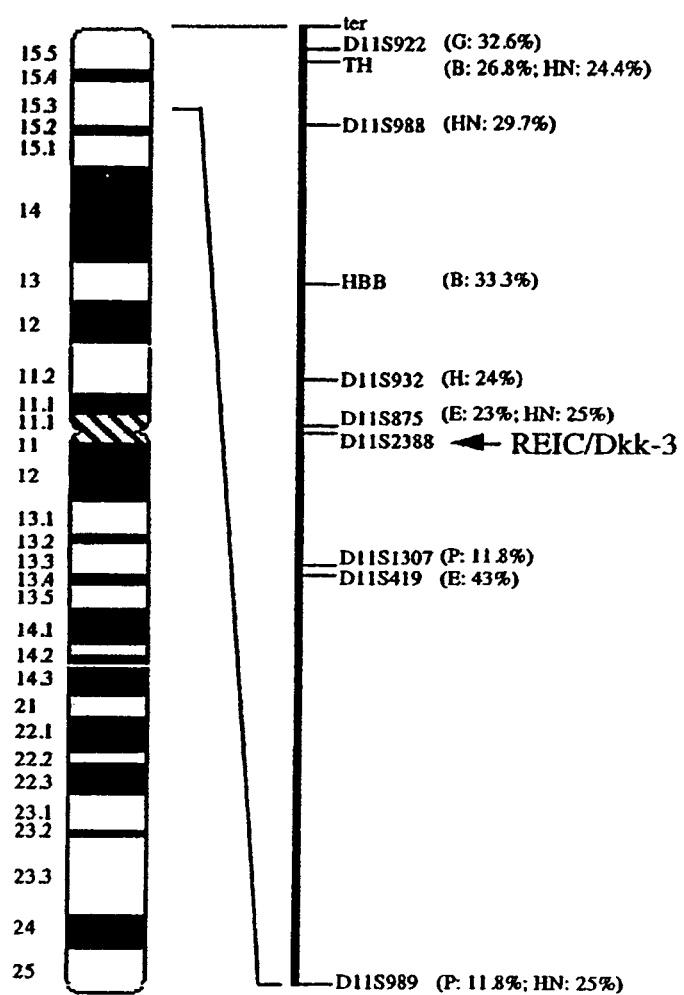
FIG. 9 is a map of human chromosome 11. In the map at 11p15 there are shown LOH frequencies (%) in various cancer tissues that have been reported and the names of STS genomic markers corresponding to the respective LOHs. The cancer tissues as shown to ther with the LOH frequency values are from B (breast cancer), E (esophageal cancer), S (gastric cancer), H (hepatocellular carcinoma), HN (head and neck cancer), and P (prostate cancer).

When the base sequence of the REIC gene was compared with the STS genome marker from Gene Bank based on that information, the 3'-non-translation region of the REIC gene was confirmed to match a D11S2388 marker (genome marker for 11p15) (FIGS. 10 and 11). These results revealed that the REIC gene was located in 11p15. As shown in FIG. 9, the LOH frequencies in various cancer tissues have been quoted from the following references: for breast cancer (B) Winqvist, R. et. al., Cancer Res., 53, 4486, 1993; for esophageal cancer (E) Dolan, K., et al., Br. J. Cancer, 78, 950, 1988; for gastric cancer (G) Baffa, R., et al., Cancer Res., 56, 268, 1996; for hepatocellular carcinoma (H) Sheu, J-C., et al., Br. J. cancer, 80, 468, 1999; for head and neck cancer El-Naggar, A. K., et al., Clin. Cancer res., 2, 903, 1996; for prostate cancer (P) Dahiya, R., et al., Int. J. Cancer, 72, 283, 1997.

Example 11

Expression of REIC Gene in Clinical Samples

1. Availability of Clinical Samples

Various cancerous and non-cancerous tissues were made available from 34 patients who had been operated at the School of Medicine, Okayama University under informed consent.

2. Expression of the REIC Gene

Figure 11A:
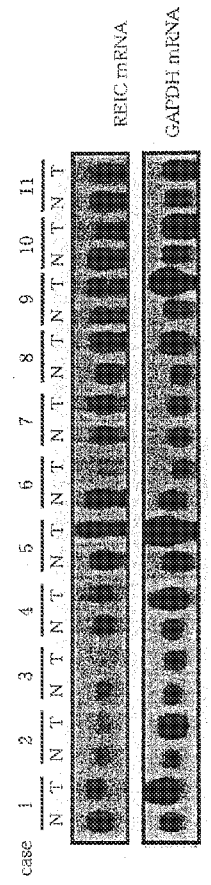
FIG. 11A is a representation corresponding to an autoradiograph showing the results of Northern blotting when the expression of the REIC gene in the tissues from a group of patients with non-small-cell lung cancer were examined. "N" indicates a non-cancerous tissue and "T" indicates a cancerous tissue.
Figure 11B:
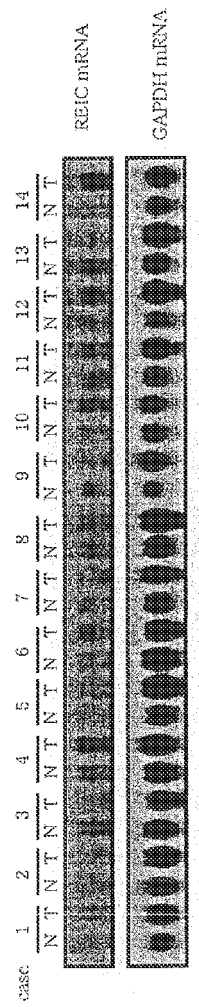
FIG. 11B is a representation corresponding to an autoradiograph showing the results of Northern blotting when the expression of the REIC gene in the tissues from a group of patients with hepatocellular carcinoma were examined. "N" indicates a non-cancerous tissue and "T" indicates a cancerous tissue.
Figure 11E:
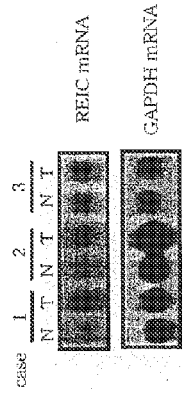
FIG. 11E is a representation corresponding to an autoradiograph showing the results of Northern blotting when the expression of the REIC gene in the tissues from a plurality of patients with colon cancer were examined. "N" indicates a non-cancerous tissue and "T" indicates a cancerous tissue.
Figure 11D:
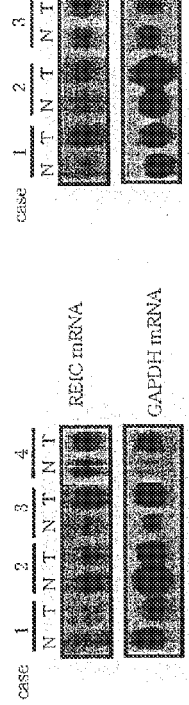
FIG. 11D is a representation corresponding to an autoradiograph showing the results of Northern blotting when the expression of the REIC gene in the tissues from a plurality of patients with gastric cancer were examined. "N" indicates a non-cancerous tissue and "T" indicates a cancerous tissue.
Figure 11C:
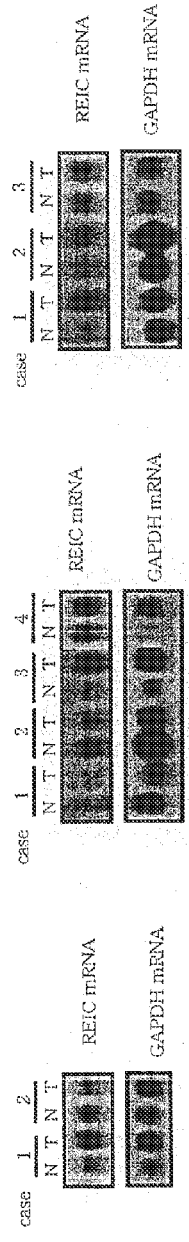
FIG. 11C is a representation corresponding to an autoradiograph showing the results of Northern blotting when the expression of the REIC gene in the tissues from a plurality of patients with esophageal cancer were examined. "N" indicates a non-cancerous tissue and "T" indicates a cancerous tissue.

Total RNA was recovered from the cancerous and non-cancerous tissues made available in 1 above by the guanidine-thiocyanate method. The total RNA (10 µg) was electrophoresed on 1% formaldehyde/agarose gel and fixed on a nitrocellulose film (Hybribond N+ available from Amersham Pharmacia Biotech Inc.). Next, a probe labeled with ($\alpha$-$^{32}$P)-dCTP was used to carry out Northern hybridization of the REIC cDNA fragment (at 42° C. for 12 hours). The membrane was placed in a buffer containing 5×SSC, 50% formamide, 1×Denhart solution, 0.2% SDS, 20 mM sodium phosphate, and thermally denatured salmon sperm DNA (100 µg/ml); and to this was added probe DNA labeled with a radioisotope and hybridized at 65° C. Subsequently, the filter was washed in 2×SSC/0.5% SDS buffer at 55° C. and in 0.1×SSC/0.5% SDS buffer at 55° C. once again. Autoradiography was carried out on an X-ray film. Consequently, the expressed amount of the REIC gene was reduced in the following cases: ten out of eleven cases with non-small-cell lung cancer patients (FIG. 11A, cases 1-6 and 8-11); four out of thirteen cases with hepatocellular carcinoma patients (FIG. 11B, cases 8, 9, 11, and 13); one out of two cases with esophageal cancer patients (FIG. 11C, case 2); and one out of four cases with gastric cancer patients (FIG. 11D, case 4). On the other hand, reduction in the expressed amount of the REIC gene was not noted in three cases of the colon cancer patients (FIG. 11E).

Example 12

RFLP Analysis of REIC Gene

Restriction fragment length polymorphism analysis (RFLP) was performed to carry out variation analysis of the REIC gene. Chromosomal DNAs were recovered from hepatocellular carcinoma-derived cell lines, JHH-1, HuH-6, HepG2, HLE, HuH-7, PLC/PRC/5, Hep3B, JHH-7, JHH-2, JHH-6, JHH-4, and JHH-5 according to the method described below. Chromosomal DNA was recovered from normal fibroblasts KMS-6 as a positive control.

1. Recovery of Chromosomal DNA

The respective cells that had been grown in a confluent manner were recovered from two culturing plates by trypsin treatment. The recovered cells were suspended in 1×TEN buffer [TEN: 50 mM Tris-HCl (pH 8.0), 1 mM EDTA, 100 mM NaCl] and homogenized. To the homogenized suspension were added 750 µl of SDS (10%) and proteinase K (20 mg/ml available from Merck AG) providing 500 µg/µl. Gentle inverted mixing was done and after incubation at 55° C. for 1 hour, the incubation continued at 37° C. overnight. Phenol/chloroform extraction was carried out twice and the recovered supernatant was further subjected to phenol/chloroform extraction twice, whereby a supernatant was recovered. To the recovered supernatant was added 10.2 ml of ethanol preserved at −20° C. and mixed. The resulting filamentous DNA was removed with a Pasteur pipette and excess ethanol was removed and dried. To the dried DNA was added TE buffer [10 mM Tris-HCl (pH 8.0), 1 mM EDTA] and mixed at room temperature for 1 to 2 days to dissolve DNA.

2. RFLP Analysis

Figure 12:
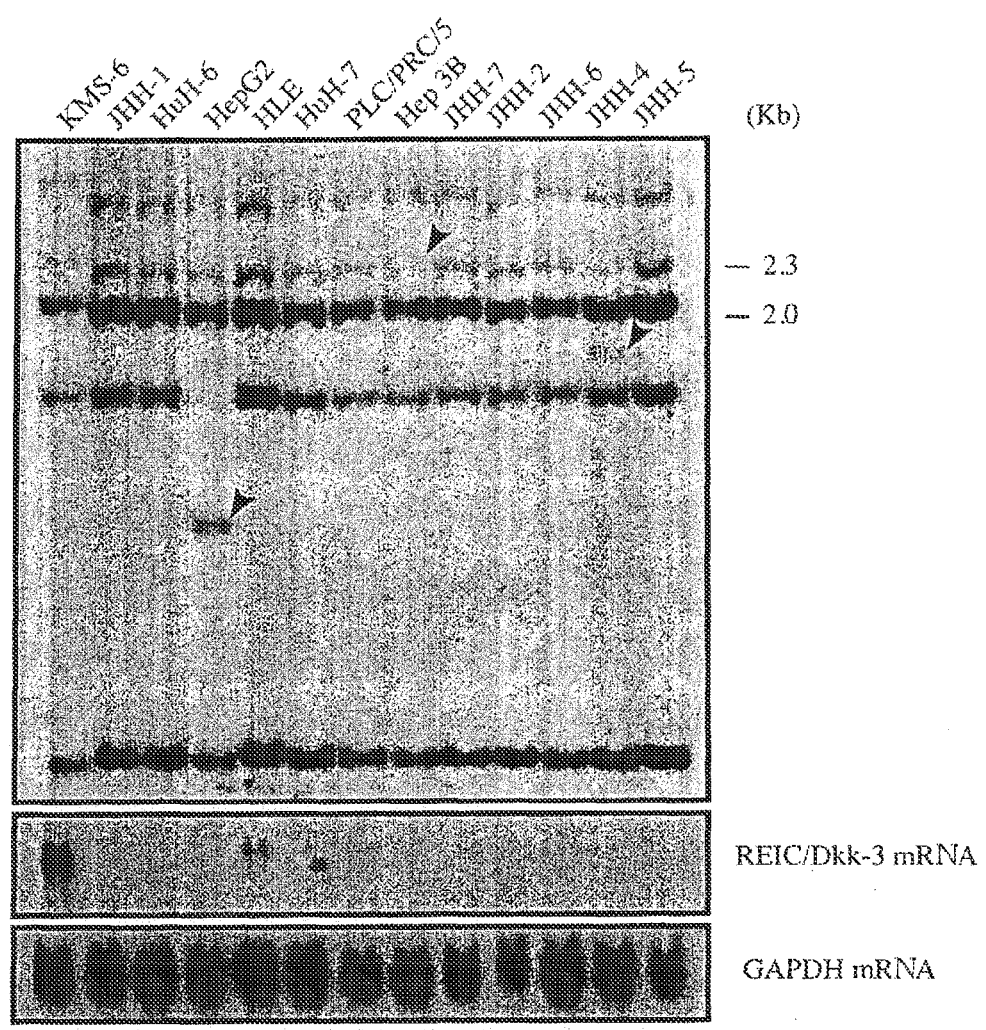
FIG. 12 is a representation corresponding to an autoradiograph showing the results of Southern blotting when an RFLP analysis of the REIC gene in various cell lines derived from the hepatoma was carried out.

DNA recovered in 1 was digested with restriction enzyme PstI and was electrophoresed on 1% agarose gel; and it was fixed onto a nitrocellulose film (Hybribond N+ available from Amersham Pharmacia Biotech Inc.). Next, a probe (the full-length of the REIC cDNA fragment as described in SEQ ID NO:3) labeled with ($\alpha$-$^{32}$P)-dCTP was used to carry out Southern hybridization (at 42° C. for 12 hours). The membrane was placed in a buffer containing 5×SSC, 50% formamide, 1×Denhart solution, 0.2% SDS, 20% sodium phosphate, and thermally denatured salmon sperm DNA (100 µg/ml); and to this was added probe DNA labeled with a radioisotope and hybridized at 65° C. Subsequently, the filter was washed in 2×SSC/0.5% SDS buffer at 55° C. and in 0.1×SSC/0.5% SDS buffer at 55° C. once again. Autoradiography was carried out on an X-ray film. Consequently, it was confirmed that allele disappeared in the three cancer cell lines of HepG2, Hep3B, and JHH-4. This suggests the possibility that not only the expression of the REIC gene was reduced, but also the REIC gene itself experienced LOH (FIG. 12).

Example 13

Involvement of REIC Gene in Cell Cycle

Figure 13A:
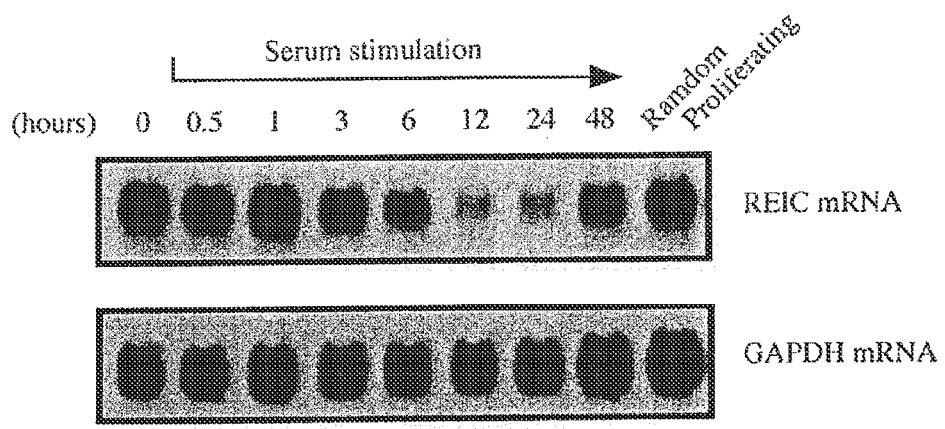
FIG. 13A is a representation corresponding to an autoradiograph showing the results of Northern blotting when changes in the expressed amount of the REIC gene at the cell cycle of KMS-6 were examined.
Figure 13B:
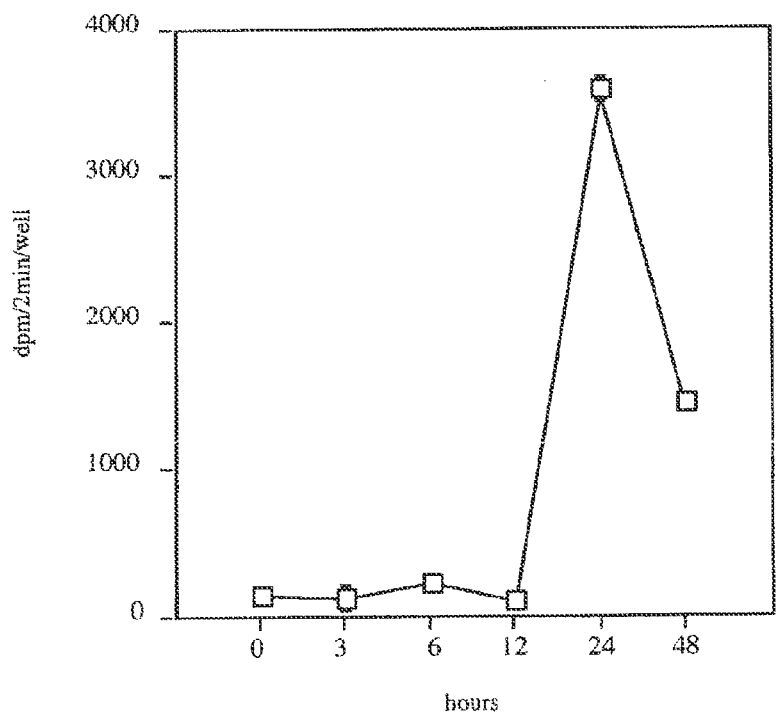
FIG. 13B is a graph showing the test results of $^3$H thymidine incorporation into KMS-6 cells at the cell cycle of KMS-6 similarly to FIG. 13A.

To identify changes in the expressed amount of the REIC gene in a cell cycle, the following experiment was conducted. KMS-6 cells were inoculated in a 10-cm Petri dish at $2\times10^6$ cell/dish. The medium was prepared so as to provide a serum concentration therein of 0.5% during inoculation. Cultivation was carried out for 72 hours and the cell cycle was synchronized to a G0 phase (resting state). The serum was next added to provide a level of 10% and the cell cycle was allowed to start by stimulating the cells. Total RNA 0, 0.5, 1, 3, 6, 12, 24, or 48 hours after addition was recovered and total RNA from the normal culturing conditions was recovered, which were analyzed for changes in the expressed amount of the REIC gene using Northern hybridization. Consequently, it was confirmed that the expression of REIC gene was reduced most 12 hours after addition of the serum and then it increased again. The change in the expressed amount of the GAPDH gene was analyzed as the control; and as a result, it was confirmed that a constant amount of expression was throughout regardless of the cell cycle (FIG. 13A). Simultaneously, when $^3$H thymidine incorporation was determined following Example 7-2, it was confirmed that the $^3$H thymidine incorporation increased 24 hours after addition of the serum and it decrearsed again thereafter (FIG. 13B).

From the foregoing results it is thought that the REIC gene is expressed strongly at G0 phase in the cell cycle to act toward stopping cell proliferation, whereas it acts toward directing the cell cycle to G1 phase with decreasing its expression.

Example 14

Induction of Expression of REIC Gene by a Cell Proliferation Inhibitor

Figure 14:
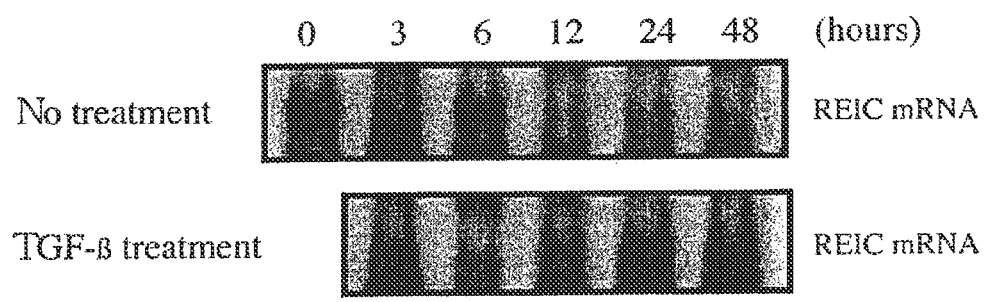
FIG. 14 is a representation corresponding to an autoradiograph showing the results of Northern blotting when changes in the expressed amount of the REIC gene in the presence or absence of TGF-β were compared.

JHH-1 cells were inoculated in a 10-cm Petri dish at $2\times10^6$ cell/dish. TGF-β, an epithelial cell proliferation inhibitor, was next added to the culture of JHH-1 cells, providing a level of 2.5 ng/ml. Total RNA prior to the addition of TGF-β, 3, 6, 12, 24, or 48 hours after its addition was recovered and total RNA from the normal culturing conditions was recovered. When the recovered RNAs were analyzed by Northern hybridization, it was confirmed that the expression of REIC gene increased 24 hours after the addition of TGF-β (FIG. 14).

From the foregoing results it is thought that since a cell proliferation inhibitory effect can be expected for a compound capable of inducing the expression of the REIC gene, the expression of the REIC gene will be useful in screening candidate low molecular weight compounds for cancer therapy.

Example 15

Preparation of pAxCaREIC Cosmid Vector

Figure 15:
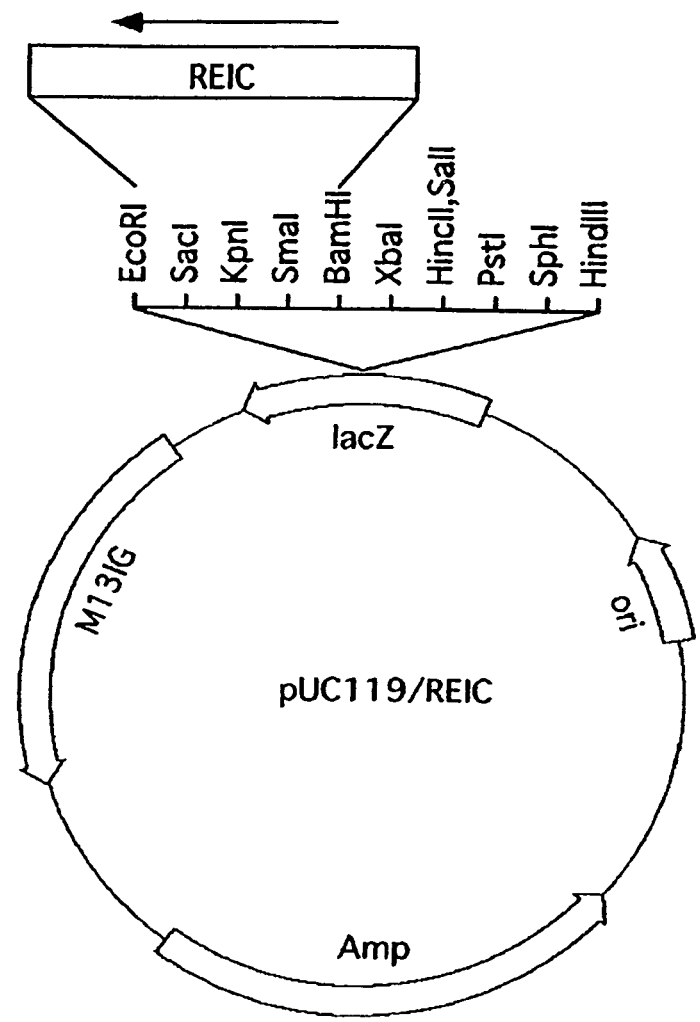
FIG. 15 is a schematic representation showing the construction of a pUC119/REIC expression plasmid used in this invention.
Figure 16:
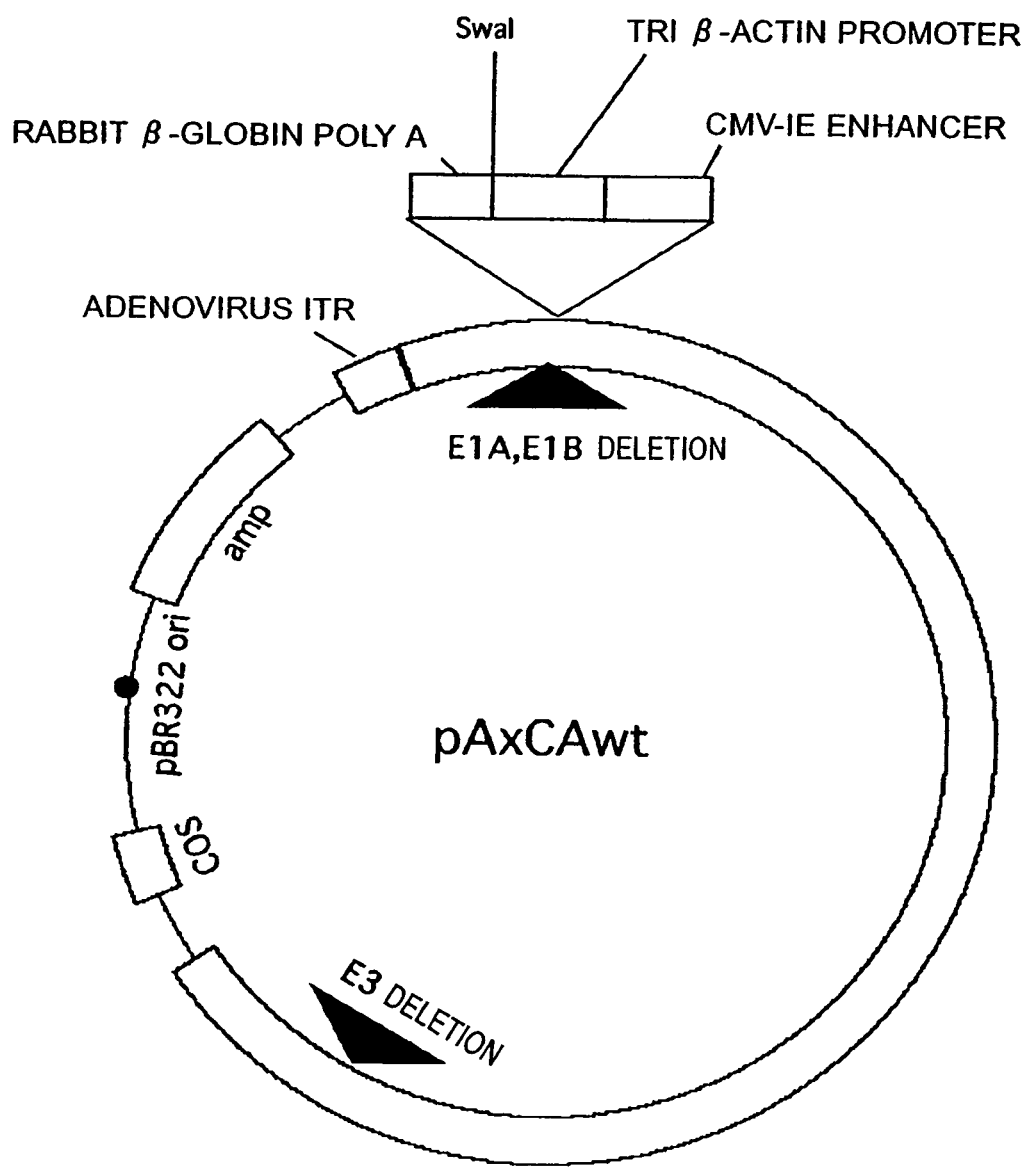
FIG. 16 is a schematic representation showing the construction of a pAxCAwt cosmid used in this invention.
Figure 17:
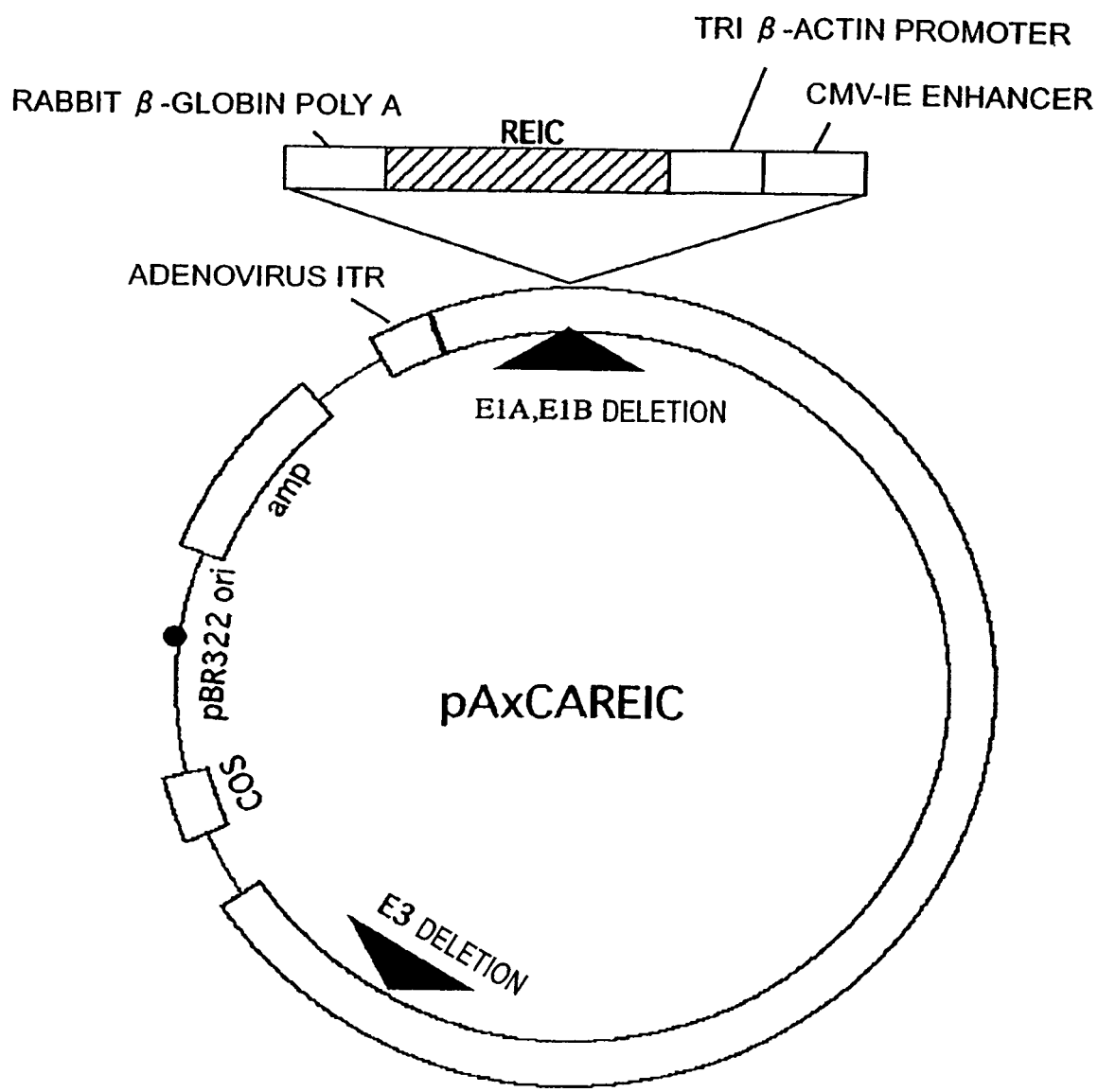
FIG. 17 is a schematic representation showing the construction of a pAxCAREIC cosmid vector used in this invention.

Primers were designed: a primer wherein a BamHI site was designed before the start codon of REIC (REICS: 5'-GGATC-CAGAGCGGAAATGCAGCGG-3' (SEQ ID NO:10) sequence obtained by linking a BamHI site of GGATCC to the 5'-end of a sequence corresponding to base nos. 190 to 206 in SEQ ID NO:4) and a primer (REICA: 5'-GAAT-TCTAAATCTCTTCCCCTCCCAG-3' (SEQ ID NO:11) sequence obtained by linking an EcoRI site of GAATTC to the 5'-end of the antisense strand of a sequence corresponding to base nos. 1230 to 1249 in SEQ ID NO:4). pTracer/REIC was next used as a template to amplify the coding region of REIC through PCR. The PCR conditions were such that 30 cycles were conducted at 94° C. for 30 seconds, 63° C. for 30 seconds and 72° C. for 1 minute. After an about 1.1 kb amplified product was recovered from the gel and digested with EcoRI and BamHI, it was subcloned into pUC119. This was introduced into E. coli. DH5α. The base sequence of a plasmid extracted from ampicilin-resistant clones was analyzed, and it was confirmed that there was no variation introduced in the insert sequence (pUC119/REIC in FIG. 15). PUC119/REIC was digested with EcoRI and BamI to recover an about 1.1 kb REIC fragment. The recovered REIC fragment was made blunt at their ends using a DNA Blunting Kit (Takara Shuzo Co. Ltd.), and was subcloned into the SWaI site of a cosmid containing a CAG promoter (pAxCAwt in FIG. 16). The resulting cosmid (pAxCAREIC in FIG. 17) was digested with ClaI to determine the presence or absence of insert. Furthermore, the cosmid was digested with StuI and SpeI, confirming that the direction of the insert was 5'-promoter-insert-polyA signal.

Example 16

Preparation of Recombinant Adenovirus Vector for Expression of REIC

Figure 18:
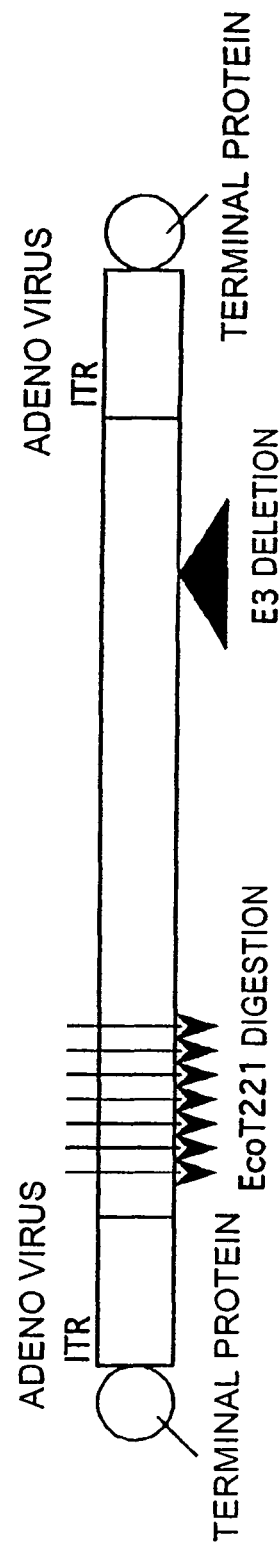
FIG. 18 is a schematic representation showing the treatment of Adenovirus to prepare an Adenovirus vector used in this invention.

A recombinant Adenovirus vector for the expression of REIC was prepared according to the COS-TPC method (Miyake, S., et al., Proc. Natl. Acad. Sci. USA., 93, 1320, 1966).

pAxCAREIC prepared in Example 15 (8 µg) and COS-TPC treated with EcoT22I (5 µg) were subjected to transfection into 293 cells by the calcium phosphate method (FIG. 18). After culturing at 37° C. for 12 hours under 5% $CO_2$ conditions, the cells were inoculated on a 96-well plate and were further cultured for 10 to 15 days. The culture was recovered together with dead cells from the well where the cells were dead. After six times of freeze-thaw, the supernatant centrifuged at 5,000 rpm for 5 minutes was stored as a primary virus solution at −80° C. 293 cells and HeLa cells were infected with the primary virus solution. Three days later, HeLa cells showed no cell degeneration and culture was recovered together with dead cells from the clone where 293 cells were dead completely. After six times of freeze-thaw, the supernatant was stored as a secondary virus solution at −80° C. Following the method described in Example 12-1, chromosomal DNA was prepared from the cells obtained when the secondary virus solution was prepared. After digestion with XhoI and ClaI, this DNA was subjected to agarose electrophoresis and the presence or absence of the REIC gene was determined.

293 cells were infected with the secondary virus solution of the clone selected by these manipulations. When the cells were dead, culture was recovered together with the dead cells.

After six times of freeze-thaw, the supernatant centrifuged at 3,000 rpm for 10 minutes was stored as a tertiary virus solution at −80° C. Scale up was conducted through similar manipulations to finally prepare a quaternary virus solution, which was stored at −80° C. (Adeno-REIC).

Example 17

Determination of the Presence or Absence of Contamination by Wild-Type Adenovirus HeLa cells were infected with the quaternary virus solution produced in Example 16. Three days later chromosomal DNA was prepared according to the method described in Example 12-1. The prepared DNA was used as a template to carry out 25-cycle PCR reaction by employing a primer set designed to amplify from the start codon to the 3'-end of the first exon of the E1A gene (5'-ATGAGACATATTATCTGCCACGGAG-GTGTTATTAC-3' (SEQ ID NO: 12), 5'-CCTCTTCATC-CTCGTCGTCACTGGGTGGAAAGCCA-3' (SEQ ID NO:13). After PCR, electrophoresis on agarose gel was conducted to determine the presence or absence of an E1A gene fragment (214 bp).

Example 18

Determination of Gene Transfer Efficiency of Adeno-REIC

The titer of Adeno-REIC was measured according to $TCID_{50}$ method (50% tissue culture infectious dose). Adeno-REIC prepared in Example 16 was diluted serially 10-fold to prepare a $10^4$-fold virus dilution. The $10^4$-fold virus dilution was transferred to the first column of a 96-well plate. Then 3" dilution was carried out up till the eleventh column and finally, from $10^4$- to $3^{11}$-virus dilutions were prepared. The 12th column was made the control for non-infected cells. After 293 cells were inoculated at $3 \times 10^4$ cells/well, cultivation was carried out at 37° C. for 11 to 13 days under 5% $CO_2$ conditions to determine the presence or absence of cell degeneration. $TCID_{50}$ was calculated statistically according to the Karber equation, and consequently, the titer of Adeno-REIC was determined to be $6.6 \times 10^9$ pfu/ml.

INDUSTRIAL APPLICABILITY

As described above, the genes according to this invention and the proteins encoded by the genes according to this invention both experience their reduced expression or their disappearance in immortal cells including cancer cells; therefore, they will prove to be effective markers for the diagnosis of diseases caused by the proliferation of those cells and thus can be used as diagnostic agents such as cancer diagnostics.

Also, the proteins according to this invention posses cell proliferation inhibitory activity; therefore, they are useful for the treatment of diseases caused by the aberrant proliferation of cells such as cancer.

Further, the genes according to this invention express the aforementioned proteins possessing the cell proliferation inhibitory activity in a cell; therefore, they can be applied to the gene therapy, whereby they can be used in the treatment of diseases caused by the aberrant proliferation of cells.

In addition, the antisense polynucleotides of this invention stimulate the cell proliferation; therefore, they can be used in the treatment of diseases requiring the cell proliferation.

The invention claimed is:

1. A method of decreasing proliferation of cancer cells comprising;
   (a) incorporating a polynucleotide comprising the DNA sequence set forth in SEQ ID NO: 2 or a polynucleotide encoding the amino acid sequence set forth in SEQ ID NO: 1 operably linked to a promoter into a cosmid, or plasmid or a recombinant vector; and directly administering to the cancer cells, wherein the cancer cells contain active WNT, the cosmid, plasmid or recombinant vector into cancer cells effective to decrease proliferation of said cancer cells and WNT remains active.

2. The method according to claim 1, wherein said polynucleotide consists essentially of the DNA sequence set forth in SEQ ID NO:2.

3. The method according to claim 2, wherein the DNA is contained in a viral vector.

4. The method according to claim 3, wherein the viral vector is an Adenovirus vector.

5. The method according to claim 1, wherein the cancerous cell(s) are lung cancer, hepatocellular carcinoma, esophageal cancer or gastric cancer cell(s).

6. The method according to claim 1, wherein said polynucleotide consists essentially of the DNA sequence encoding the amino acid sequence set forth in SEQ ID NO:1.

7. A method of treating cancer in a human patient comprising:
   (a) incorporating a polynucleotide selected from the group comprising a polynucleotide comprising the DNA sequence set forth in SEQ ID NO: 2 or a polynucleotide encoding the amino acid sequence set forth in SEQ ID NO: 1 operably linked to a promoter into an expression cassette capable of gene expression in mammalian cells;
   (b) incorporating the expression cassette from (a) into a cosmid, plasmid, or virus-derived recombinant vector; and
   (c) directly administering the cosmid, plasmid, or virus-derived recombinant vector from (b) into target cancer cells in the body of the human patient, wherein said administering of the cosmid, plasmid, or virus-derived recombinant vector effective to decrease proliferation of said target cancerous cells, wherein said polynucleotide is expressed in said cancerous cells effective to reduce tumor size of said cancer and WNT remains active.

8. The method of claim 7, wherein the polynucleotide is administered into the target cancer cells via an Adenovirus vector.

9. The method of claim 7, wherein the polynucleotide is administered into the target cancer cells via a vector including a transposon.

10. The method of claim 9, wherein the vector includes a tissue specificity function.

11. A method of treating lung cancer in a patient comprising:
   (a) incorporating a polynucleotide selected from the group comprising a polynucleotide comprising the DNA sequence set forth in SEQ ID NO: 2 or a polynucleotide encoding the amino acid sequence set forth in SEQ ID NO: 1 into an expression cassette capable of gene expression in mammalian cells;
   (b) incorporating the expression cassette from (a) into a cosmid, plasmid, or virus-derived recombinant vector; and
   (c) directly administering the cosmid, plasmid, or virus-derived recombinant vector from (b) into cancerous lung cells in treating said lung cancer effective to decrease proliferation of said cancerous lung cells, wherein said polynucleotide is expressed in said cancerous cells effective to reduce lung tumor size and WNT remains active.

12. The method of claim 11, wherein the cancerous lung cells are inside the body of a patient when the polynucleotide is administered into the cancerous lung cells.

13. The method of claim 11, wherein the polynucleotide is administered into the target cancer cells via an Adenovirus vector.

14. The method of claim 11, wherein the polynucleotide is administered into the target cancer cells via a vector including a transposon.

15. The method of claim 14, wherein the vector includes a tissue specificity function.

16. The method of decreasing proliferation of cancerous cell(s) according to claim 1, wherein the cancerous cell(s) is selected from the group consisting of cancerous lung cells, cancerous cervical cells, cancerous ovarian cells, and cancerous breast cells.

17. The method of treating cancer in a human patient according to claim 7, wherein the cancer is selected from the group consisting of lung, cervical, ovarian, and breast cancer.

* * * * *

SEQUENCE LISTING

```
<160> NUMBER OF SEQ ID NOS: 16

<210> SEQ ID NO 1
<211> LENGTH: 350
<212> TYPE: PRT
<213> ORGANISM: Homo sapiens

<400> SEQUENCE: 1

Met Gln Arg Leu Gly Ala Thr Leu Leu Cys Leu Leu Leu Ala Ala Ala
1               5                   10                  15

Val Pro Thr Ala Pro Ala Pro Ala Pro Thr Ala Thr Ser Ala Pro Val
            20                  25                  30

Lys Pro Gly Pro Ala Leu Ser Tyr Pro Gln Glu Glu Ala Thr Leu Asn
        35                  40                  45

Glu Met Phe Arg Glu Val Glu Glu Leu Met Glu Asp Thr Gln His Lys
    50                  55                  60

Leu Arg Ser Ala Val Glu Glu Met Glu Ala Glu Glu Ala Ala Ala Lys
65                  70                  75                  80

Ala Ser Ser Glu Val Asn Leu Ala Asn Leu Pro Pro Ser Tyr His Asn
                85                  90                  95

Glu Thr Asn Thr Asp Thr Lys Val Gly Asn Asn Thr Ile His Val His
            100                 105                 110

Arg Glu Ile His Lys Ile Thr Asn Asn Gln Thr Gly Gln Met Val Phe
        115                 120                 125

Ser Glu Thr Val Ile Thr Ser Val Gly Asp Glu Glu Gly Arg Arg Ser
    130                 135                 140
```

His Glu Cys Ile Ile Asp Glu Asp Cys Gly Pro Ser Met Tyr Cys Gln
145                 150                 155                 160

Phe Ala Ser Phe Gln Tyr Thr Cys Gln Pro Cys Arg Gly Gln Arg Met
            165                 170                 175

Leu Cys Thr Arg Asp Ser Glu Cys Cys Gly Asp Gln Leu Cys Val Trp
            180                 185                 190

Gly His Cys Thr Lys Met Ala Thr Arg Gly Ser Asn Gly Thr Ile Cys
        195                 200                 205

Asp Asn Gln Arg Asp Cys Gln Pro Gly Leu Cys Cys Ala Phe Gln Arg
    210                 215                 220

Gly Leu Leu Phe Pro Val Cys Thr Pro Leu Pro Val Glu Gly Glu Leu
225                 230                 235                 240

Cys His Asp Pro Ala Ser Arg Leu Leu Asp Leu Ile Thr Trp Glu Leu
                245                 250                 255

Glu Pro Asp Gly Ala Leu Asp Arg Cys Pro Cys Ala Ser Gly Leu Leu
            260                 265                 270

Cys Gln Pro His Ser His Ser Leu Val Tyr Val Cys Lys Pro Thr Phe
        275                 280                 285

Val Gly Ser Arg Asp Gln Asp Gly Glu Ile Leu Leu Pro Arg Glu Val
290                 295                 300

Pro Asp Glu Tyr Glu Val Gly Ser Phe Met Glu Val Arg Gln Glu
305                 310                 315                 320

Leu Glu Asp Leu Glu Arg Ser Leu Thr Glu Glu Met Ala Leu Gly Glu
                325                 330                 335

Pro Ala Ala Ala Ala Ala Ala Leu Leu Gly Gly Glu Glu Ile
                340                 345                 350

<210> SEQ ID NO 2
<211> LENGTH: 1050
<212> TYPE: DNA
<213> ORGANISM: Homo sapiens

<400> SEQUENCE: 2
atgcagcggc ttggggccac cctgctgtgc ctgctgctgg cggcggcggt ccccacggcc      60
cccgcgcccg ctccgacggc gacctcggct ccagtcaagc ccggcccggc tctcagctac     120
ccgcaggagg aggccaccct caatgagatg ttccgcgagg ttgaggaact gatggaggac     180
acgcagcaca aattgcgcag cgcggtgaaa gagatggagg cagaagaagc tgctgctaaa     240
gcatcatcag aagtgaacct ggcaaactta cctcccagct atcacaatga ccaacaca      300 gacacgaagg ttgaaaataa taccatccat gtgcaccgag aaattcacaa gataaccaac     360
aaccagactg gacaaatggt cttttcagag acagttatca catctgtggg agacgaagaa     420
ggcagaagga gccacgagtg catcatcgac gaggactgtg gcccagcat gtactgccag     480 tttgccagct tccagtacac ctgccagcca tgccggggcc agaggatgct ctgcacccgg     540
gacagtgagt gctgtggaga ccagctgtgt gtctggggtc actgcaccaa atgcgccacc     600
aggggcagca atgggaccat ctgtgacaac cagagggact gccagccggg gctgtgctgt     660
gccttccaga gaggcctgct gttccctgtg tgcacacccc tgcccgtgga gggcgagctt     720
tgccatgacc ccgccagccg gcttctggac ctcatcacct gggagctaga gcctgatgga     780
gccttggacc gatgcccttg tgccagtggc ctcctctgcc agccccacag ccacagcctg     840
gtgtatgtgt gcaagccgac cttcgtgggg agccgtgacc aagatgggga gatcctgctg     900
cccagagagg tccccgatga gtatgaagtt ggcagcttca tggaggaggt gcgccaggag     960

```
ctggaggacc tggagaggag cctgactgaa gagatggcgc tgggggagcc tgcggctgcc   1020
gccgctgcac tgctgggagg ggaagagatt                                   1050

<210> SEQ ID NO 3
<211> LENGTH: 2660
<212> TYPE: DNA
<213> ORGANISM: Homo sapiens

<400> SEQUENCE: 3
ggcggagagg gagcctggtg ggcgggcggg gcgcgtcttg cgggctccct cgggtaccgg     60
cgctgccgca ccccgccgcg ctcccgcacc cgcggcccgc ccaccgcgcc gctcccgcat    120
ctgcacccgc agcccggcgg cctcccggcg ggagcgagca gatccagtcc ggcccgcagc    180
gcaactcggt ccagtcgggg cggcggctgc gggcgcagag cggagatgca gcggcttggg    240
gccaccctgc tgtgcctgct gctggcggcg gcggtcccca cggcccccgc gcccgctccg    300
acggcgacct cggctccagt caagcccggc ccggctctca gctacccgca ggaggaggcc    360
accctcaatg agatgttccg cgaggttgag gaactgatgg aggacacgca gcacaaattg    420
cgcagcgcgg tggaagagat ggaggcagaa gaagctgctg ctaaagcatc atcagaagtg    480
aacctggcaa acttacctcc cagctatcac aatgagacca cacagacac gaaggttgga    540 aataatacca tccatgtgca ccgagaaatt cacaagataa ccaacaacca gactggacaa    600
atggtctttt cagagacagt tatcacatct gtggagacg aagaaggcag aaggagccac    660
gagtgcatca tcgacgagga ctgtgggccc agcatgtact gccagtttgc agcttccag    720 tacacctgcc agccatgccg gggccagagg atgctctgca cccgggacag tgagtgctgt    780
ggagaccagc tgtgtgtctg gggtcactgc accaaaatgg ccaccagggg cagcaatggg    840
accatctgtg acaaccagag ggactgccag ccggggctgt gctgtgcctt ccagagaggc    900
ctgctgttcc ctgtgtgcac acccctgccc gtggagggcg agctttgcca tgacccc gcc   960 agccggcttc tggacctcat cacctgggag ctagagcctg atggagcctt ggaccgatgc    1020
ccttgtgcca gtggcctcct ctgccagccc cacagccaca gcctggtgta tgtgtgcaag    1080
ccgaccttcg tggggagccg tgaccaagat ggggagatcc tgctgccag agaggtcccc    1140 gatgagtatg aagttggcag cttcatggag gaggtgcgcc aggagctgga ggacctggag    1200
aggagcctga ctgaagagat ggcgctgggg gagcctgcgg ctgccgccgc tgcactgctg    1260
ggaggggaag agatttagat ctggaccagg ctgtgggtag atgtgcaata gaaatagcta    1320
atttatttcc ccaggtgtgt gctttaggcg tgggctgacc aggcttcttc ctacatcttc    1380
ttcccagtaa gtttcccctc tggcttgaca gcatgaggtg ttgtgcattt gttcagctcc    1440
cccaggctgt tctccaggct tcacagtctg gtgcttggga gagtcaggca gggttaaact    1500
gcaggagcag tttgccaccc ctgtccagat tattggctgc tttgcctcta ccagttggca    1560
gacagccgtt tgttctacat ggctttgata attgtttgag gggaggagat ggaaacaatg    1620
tggagtctcc ctctgattgg ttttggggaa atgtggagaa gagtgccctg ctttgcaaac    1680
atcaacctgg caaaaatgca acaaatgaat tttccacgca gttctttcca tgggcatagg    1740
taagctgtgc cttcagctgt tgcagatgaa atgttctgtt caccctgcat acatgtgtt    1800 tattcatcca gcagtgttgc tcagctccta cctctgtgcc agggcagcat tttcatatcc    1860
aagatcaatt ccctctctca gcacagcctg ggaggggggt cattgttctc ctcgtccatc    1920
agggatctca gaggctcaga gactgcaagc tgcttgccca agtcacacag ctagtgaaga    1980
ccagagcagt ttcatctggt tgtgactcta agctcagtgc tctctccact accccacacc    2040
```

| | | | |
|---|---|---|---|
| agccttggtg | ccaccaaaag | tgctccccaa aaggaaggag aatgggattt ttcttttgag | 2100 |
| gcatgcacat | ctggaattaa | ggtcaaacta attctcacat ccctctaaaa gtaaactact | 2160 |
| gttaggaaca | gcagtgttct | cacagtgtgg ggcagccgtc cttctaatga agacaatgat | 2220 |
| attgacactg | tccctctttg | gcagttgcat tagtaacttt gaaaggtata tgactgagcg | 2280 |
| tagcatacag | gttaacctgc | agaaacagta cttaggtaat tgtagggcga ggattataaa | 2340 |
| tgaaatttgc | aaaatcactt | agcagcaact gaagacaatt atcaaccacg tggagaaaat | 2400 |
| caaaccgagc | agggctgtgt | gaaacatggt tgtaatatgc gactgcgaac actgaactct | 2460 |
| acgccactcc | acaaatgatg | ttttcaggtg tcatggactg ttgccaccat gtattcatcc | 2520 |
| agagttctta | aagtttaaag | ttgcacatga ttgtataagc atgctttctt tgagttttaa | 2580 |
| attatgtata | aacataagtt | gcatttagaa atcaagcata aatcacttca actgctaaaa | 2640 |
| aaaaaaaaaa | aaaaaaaaa | | 2660 |

<210> SEQ ID NO 4
<211> LENGTH: 2632
<212> TYPE: DNA
<213> ORGANISM: Homo sapiens

<400> SEQUENCE: 4

| | | | |
|---|---|---|---|
| gaggtagggg | ctgagagagg | cttgaggtgg aagtgggggt cggcactct gacctggtcg | 60 |
| aggaggggct | agggtttgaa | ccggggacag agtctaggtg agctggggct gggagctatt | 120 |
| agcgtagagg | atccgggttc | ggttgctctg gcgagggctc cagcatcaca ggcggcggct | 180 |
| gcgggcgcag | agcggagatg | cagcggcttg gggccaccct gctgtgcctg ctgctggcgg | 240 |
| cggcggtccc | cacggccccc | gcgcccgctc cgacggcgac ctcggctcca gtcaagcccg | 300 |
| gcccggctct | cagctacccg | caggaggagg ccaccctcaa tgagatgttc cgcgaggttg | 360 |
| aggaactgat | ggaggacacg | cagcacacaaat tgcgcagcgc ggtggaagag atggaggcag | 420 |
| aagaagctgc | tgctaaagca | tcatcagaag tgaacctggc aaacttacct cccagctatc | 480 |
| acaatgagac | caaacagac | acgaaggttg gaaataatac catccatgtg caccgagaaa | 540 |
| ttcacaagat | aaccaacaac | cagactggac aaatggtctt ttcagagaca gttatcacat | 600 |
| ctgtgggaga | cgaagaaggc | agaaggagcc acgagtgcat catcgacgag gactgtgggc | 660 |
| ccagcatgta | ctgccagttt | gccagcttcc agtacacctg ccagccatgc cggggccaga | 720 |
| ggatgctctg | cacccgggac | agtgagtgct gtggagacca gctgtgtgtc tggggtcact | 780 |
| gcaccaaaat | ggccaccagg | ggcagcaatg ggaccatctg tgacaaccag agggactgcc | 840 |
| agccggggct | gtgctgtgcc | ttccagagag gcctgctgtt ccctgtgtgc acacccctgc | 900 |
| ccgtggaggg | cgagctttgc | catgaccccg ccagccggct tctggacctc atcacctggg | 960 |
| agctagagcc | tgatggagcc | ttggaccgat gcccttgtgc cagtggcctc ctctgccagc | 1020 |
| cccacagcca | cagcctggtg | tatgtgtgca agccgacctt cgtggggagc cgtgaccaag | 1080 |
| atgggagat | cctgctgccc | agagaggtcc ccgatgagta tgaagttggc agcttcatgg | 1140 |
| aggaggtgcg | ccaggagctg | gaggacctgg agaggagcct gactgaagag atggcgctgg | 1200 |
| gggagcctgc | ggctgccgcc | gctgcactgc tgggagggga agagatttag atctggacca | 1260 |
| ggctgtgggt | agatgtgcaa | tagaaatagc taatttattt ccccaggtgt gtgctttagg | 1320 |
| cgtgggctga | ccaggcttct | tcctacatct tcttcccagt aagtttcccc tctggcttga | 1380 |
| cagcatgagg | tgttgtgcat | ttgttcagct cccccaggct gttctccagg cttcacagtc | 1440 |

-continued

```
tggtgcttgg gagagtcagg cagggttaaa ctgcaggagc agtttgccac ccctgtccag    1500
attattggct gctttgcctc taccagttgg cagacagccg tttgttctac atggctttga    1560
taattgtttg aggggaggag atggaaacaa tgtggagtct ccctctgatt ggttttgggg    1620
aaatgtggag aagagtgccc tgctttgcaa acatcaacct ggcaaaaatg caacaaatga    1680
attttccacg cagttctttc catgggcata ggtaagctgt gccttcagct gttgcagatg    1740
aaatgttctg ttcaccctgc attacatgtg tttattcatc cagcagtgtt gctcagctcc    1800
tacctctgtg ccagggcagc attttcatat ccaagatcaa ttccctctct cagcacagcc    1860
tggggagggg gtcattgttc tcctcgtcca tcagggatct cagaggctca gagactgcaa    1920
gctgcttgcc caagtcacac agctagtgaa gaccagagca gtttcatctg gttgtgactc    1980
taagctcagt gctctctcca ctaccccaca ccagccttgg tgccaccaaa agtgctcccc    2040
aaaaggaagg agaatgggat ttttcttttg aggcatgcac atctggaatt aaggtcaaac    2100
taattctcac atccctctaa aagtaaacta ctgttaggaa cagcagtgtt ctcacagtgt    2160
ggggcagccg tccttctaat gaagacaatg atattgcac tgtccctctt tggcagttgc    2220
attagtaact ttgaaaggta tatgactgag cgtagcatac aggttaacct gcagaaacag    2280
tacttaggta attgtagggc gaggattata atgaaatttt gcaaaatcac ttagcagcaa    2340
ctgaagacaa ttatcaacca cgtggagaaa atcaaaccga gcagggctgt gtgaaacatg    2400
gttgtaatat gcgactgcga acactgaact ctacgccact ccacaaatga tgttttcagg    2460
tgtcatggac tgttgccacc atgtattcat ccagagttct taaagtttaa agttgcacat    2520
gattgtataa gcatgctttc tttgagtttt aaattatgta taaacataag ttgcatttag    2580
aaatcaagca taaatcactt caactgctaa aaaaaaaaaa aaaaaaaaa aa            2632
```

<210> SEQ ID NO 5
<211> LENGTH: 266
<212> TYPE: DNA
<213> ORGANISM: Homo sapiens

<400> SEQUENCE: 5

```
cattttcata tccaagatca attccctctc tcagcacagc ctggggaggg ggtcattgtt     60
ctcctcgtcc atcagggatc tcagaggctc agagactgca agctgcttgc ccaagtcaca    120
cagctagtga agaccagagc agtttcatct ggttgtgact ctaagctcag tgctctctcc    180 actacccccac accagccttg gtgccaccaa aagtgctccc caaaaggaag gagaatggga    240
tttttctttt gaggcatgca catctg                                         266
```

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 6

```
tggatccatg cagcggcttg gggccac                                         27
```

<210> SEQ ID NO 7
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 7
tgaattcaat ctcttcccct cccagcag                                           28

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gatttagatc tggaccaggc                                                    20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ctgagcaaca ctgctggatg                                                    20

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ggatccagag cggaaatgca gcgg                                               24

<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gaattctaaa tctcttcccc tcccag                                             26

<210> SEQ ID NO 12
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
atgagacata ttatctgcca cggaggtgtt attac                                   35

<210> SEQ ID NO 13
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 13
cctcttcatc ctcgtcgtca ctgggtggaa agcca                                  35

<210> SEQ ID NO 14
<211> LENGTH: 19
<212> TYPE: PRT
<213> ORGANISM: Homo sapiens

<400> SEQUENCE: 14

Lys Leu Ala Ala Ser Trp Arg Arg Cys Ala Arg Ser Trp Arg Thr Trp
1               5                   10                  15

Arg Gly Ala

<210> SEQ ID NO 15
<211> LENGTH: 203
<212> TYPE: DNA
<213> ORGANISM: Homo sapiens

<400> SEQUENCE: 15
aatatgcgac tgcgaacact gaactctacg ccactccaca aatgatgttt tcaggtgtca       60
tggactgttg ccaccatgta ttcatccaga gttcttaaag tttaaagttg cacatgattg      120
tataagcatg ctttctttga gttttaaatt atgtataaac ataagttgca tttagaaatc      180
aagcataaat cacttcaact gct                                              203

<210> SEQ ID NO 16
<211> LENGTH: 203
<212> TYPE: DNA
<213> ORGANISM: Homo sapiens
<220> FEATURE:
<221> NAME/KEY: modified_base
<222> LOCATION: (73)..(73)
<223> OTHER INFORMATION: a, c, t, g, unknown or other

<400> SEQUENCE: 16
aatatgcgac tgcgaacact gaactctacg ccactccaca aatgatgttt tcaggtgtca       60
tggactgttg ccnccatgta ttcatccaga gttcttaaag tttaaagttg cacatgattg      120
tataagcatg ctttctttga gttttaaatt atgtataaac ataagttgca tttagaaatc      180
aagcataaat cacttcaact gct                                              203
```